US010668190B2

(12) United States Patent
Milbocker et al.

(10) Patent No.: US 10,668,190 B2
(45) Date of Patent: Jun. 2, 2020

(54) MULTIPHASE GEL

(71) Applicant: BVW Holding AG, Cham (CH)

(72) Inventors: Michael Milbocker, Holliston, MA (US); Lukas Bluecher, Eurasburg (DE)

(73) Assignee: BVW Holding AG, Cham (CH)

( * ) Notice: Subject to any disclaimer, the term of this patent is extended or adjusted under 35 U.S.C. 154(b) by 129 days.

(21) Appl. No.: 15/586,114

(22) Filed: May 3, 2017

(65) Prior Publication Data

US 2017/0319751 A1 Nov. 9, 2017

Related U.S. Application Data

(60) Provisional application No. 62/331,286, filed on May 3, 2016.

(51) Int. Cl.
*A61L 31/04* (2006.01)
*A61L 31/12* (2006.01)
(Continued)

(52) U.S. Cl.
CPC ........... *A61L 31/041* (2013.01); *A61L 31/129* (2013.01); *A61L 31/145* (2013.01); *A61L 31/148* (2013.01);
(Continued)

(58) Field of Classification Search
CPC .... A61L 31/041; A61L 31/129; A61L 31/145; A61L 31/148; A61L 31/16;
(Continued)

(56) References Cited

U.S. PATENT DOCUMENTS

| 6,312,725 B1 | 11/2001 | Wallace et al. |
| 6,399,700 B2 | 6/2002 | Mayes et al. |
| 6,413,539 B1 | 7/2002 | Shalaby |

(Continued)

FOREIGN PATENT DOCUMENTS

| WO | 2007089484 A2 | 8/2007 |
| WO | 2010114785 A1 | 10/2010 |

(Continued)

OTHER PUBLICATIONS

International Search Report and Written Opinion for corresponding International Patent Application No. PCT/2017/030892, dated Jul. 27, 2017, 289 pages.

*Primary Examiner* — Trevor Love
(74) *Attorney, Agent, or Firm* — Patterson Intellectual Property Law, P.C.

(57) ABSTRACT

Disclosed are hydrogels polymerized with or around a solid biofunctional moiety, biodegradable or permanent, designed to be implantable in a mammalian body, intended to block or mitigate the formation of tissue adhesions, and intended to aid in functional healing. The hydrogels of the present invention are characterized by comprising multiphasic structural elements: a) at least one gel phase, b) at least one solid phase, c) optional polymeric chains connecting gel and solid phases, d) optional shape designs that provide for an interpenetrating geometry between gels and solids, e) optional shape designs that enhance a tissue-hydrogel interface, and f) optional shape designs that provide a biofunctional aspect. The hydrophobicity of the various phases is chosen to reduce tissue adhesion and enhance tissue healing. The morphology of the polymers comprising the gel phase is typically of high molecular weight and has morphology that encourages entanglement. Useful polymeric structures include branching chains, comb or brush, and dendritic morphologies.

14 Claims, 4 Drawing Sheets

(51) Int. Cl.
*A61L 31/14* (2006.01)
*A61L 31/16* (2006.01)
*C08L 75/06* (2006.01)
*C08L 75/08* (2006.01)

(52) U.S. Cl.
CPC .............. *A61L 31/16* (2013.01); *C08L 75/06* (2013.01); *C08L 75/08* (2013.01); *A61L 2300/30* (2013.01); *A61L 2300/41* (2013.01); *A61L 2300/412* (2013.01); *A61L 2300/424* (2013.01); *A61L 2300/802* (2013.01); *A61L 2400/18* (2013.01); *C08L 2201/06* (2013.01); *C08L 2203/02* (2013.01)

(58) Field of Classification Search
CPC ........... A61L 2300/424; A61L 2300/30; A61L 2300/802; A61L 2400/18; C08L 75/06; C08L 75/08; C08L 2201/06; C08L 2203/02
See application file for complete search history.

(56) References Cited

U.S. PATENT DOCUMENTS

| | | |
|---|---|---|
| 6,465,513 B1 | 10/2002 | Grant et al. |
| 6,486,140 B2 | 11/2002 | Hansson et al. |
| 6,486,285 B2 | 11/2002 | Fujita |
| 6,514,522 B2 | 2/2003 | Domb |
| 6,642,363 B1 | 11/2003 | Mooney et al. |
| 6,903,199 B2 | 6/2005 | Moon et al. |
| 6,923,961 B2 | 8/2005 | Liu et al. |
| 7,026,284 B2 | 4/2006 | Gen |
| 7,265,098 B2 | 9/2007 | Miller et al. |
| 7,316,845 B2 | 1/2008 | Hubbell et al. |
| 7,569,643 B2 | 8/2009 | Cohn et al. |
| 7,879,356 B2 | 2/2011 | Cohn et al. |
| 7,883,694 B2 | 2/2011 | Rhee et al. |
| 7,994,116 B2 | 8/2011 | Olmarker |
| 8,003,782 B1 | 8/2011 | Brown et al. |
| 8,048,444 B2 | 11/2011 | Calhoun et al. |
| 2009/0012462 A1 | 1/2009 | Milbocker et al. |
| 2009/0208589 A1 | 8/2009 | Grinstaff et al. |
| 2009/0222038 A1 | 9/2009 | Fitz et al. |
| 2010/0160960 A1 | 6/2010 | Wagman et al. |
| 2011/0166089 A1 | 7/2011 | Suzuki et al. |
| 2011/0237542 A1 | 9/2011 | Cho et al. |
| 2011/0243883 A1 | 10/2011 | Grinstaff et al. |
| 2013/0095161 A1 | 4/2013 | Bluecher et al. |
| 2014/0301971 A1 | 10/2014 | Milbocker et al. |
| 2017/0021053 A1 | 1/2017 | Bluecher et al. |

FOREIGN PATENT DOCUMENTS

| | | |
|---|---|---|
| WO | 2012006720 A1 | 1/2012 |
| WO | 2012177825 A1 | 12/2012 |
| WO | 2013052779 A2 | 4/2013 |
| WO | 2013112381 A2 | 8/2013 |

MULTIPHASE GEL

CROSS-REFERENCES TO RELATED APPLICATIONS

This application claims benefit of U.S. provisional application No. 62/331,286 filed on May 3, 2016, which is hereby incorporated by reference in its entirety.

TECHNICAL FIELD

The present disclosure relates generally to biomedical and pharmaceutical applications of absorbable or biodegradable multiphasic hydrogels, where optionally one or more phases are not absorbable in situ. More particularly, the present invention relates to systems of multiphase hydrogels comprising both gel and nongel phases, wherein these phases may be coupled mechanically, hydrophobically, by metal ions, or by covalent bonds.

BACKGROUND OF THE INVENTION

In connective tissue, the term "ground substance" is the non-cellular components of extracellular matrix. Cells are surrounded by extracellular matrix in tissues, which acts as a support for the cells. Ground substance traditionally does not include collagen but does include all the other proteinaceous components, including proteoglycans, matrix proteins and water. Ground substance is amorphous, gel-like, and is primarily composed of glycosaminoglycans (most notably hyaluronan), proteoglycans, and glycoproteins. The formation of tissue adhesions can best be described as a process of denaturation, and more specifically protein denaturation.

Denaturation is a process in which proteins or nucleic acids lose the tertiary structure and secondary structure which is present in their native state, by application of some external stress or compound such as an acid or base, a concentrated inorganic salt, an organic solvent, exposure to air, or temperature change.

When a surgical procedure is performed external stress is applied to tissue, which can be oxidative, change the ionic equilibrium, create necrotic byproducts, or otherwise increase the entropy of the tissue. If proteins in a living cell are denatured, this results in disruption of cell activity and possibly cell death (which occurs in all surgical procedures). Denatured proteins can exhibit a wide range of characteristics, from loss of solubility to communal aggregation. These two effects tend to create scaffolds on which bridges between living tissues are formed.

Denaturation occurs at different levels of the protein structure. In the quaternary structure denaturation, protein subunits are dissociated and/or the spatial arrangement of protein subunits is disrupted. This can lead to cell death, which promote upregulation of reaction oxygen species as well as providing an environment for microbial proliferation. The tertiary structure denaturation involves the disruption of covalent interactions between amino acid sidechains (such as disulfide bridges between cysteine groups), noncovalent dipoledipole interactions between polar amino acid sidechains, and Van der Waals (induced dipole) interactions between nonpolar amino acid sidechains. In the secondary structure denaturation, proteins lose all regular repeating patterns such as alphahelices and betapleated sheets, and adopt a random coil configuration. This contributes to the higher entropic state associated with chronic inflammation and thick capsule formation.

Primary structure denaturation, such as a sequence of amino acids held together by covalent peptide bonds, is not directly disrupted by denaturation. But the high entropy environment associated with global protein denaturation has been associated with primary structure disruption and pathologies such as cancer.

Most biological substrates lose their biological function when denatured. For example, enzymes lose their activity, because the substrates can no longer bind to the intended active site, and because amino acid residues involved in stabilizing the substrates' transition states are no longer positioned to be able to do so. The denaturing process and the associated loss of activity can be measured using techniques such as dual polarization interferometry.

Unfortunately, almost all antiadhesive materials (gel or sheet) used surgically at present are chaotropic agents. These devices disrupt the structure of macromolecules, and denature macromolecules such as proteins and nucleic acids (e.g. DNA and RNA). Chaotropic solutes increase the entropy of the system by interfering with intramolecular interactions mediated by noncovalent forces such as hydrogen bonds, van der Waals forces, and hydrophobic effects. Hydrophobic effects are primary in establishing the boundaries between tissue layers. When the equilibrium of these forces that are established in vital tissue is disrupted, the "healing" stimulus leads to macroscopic cellular structures that are deleterious to clinical success.

For these reasons it is important that antiadhesion barriers, that are, by their current construction, absorbable, not degrade into byproducts that are chaotropic. Macromolecular structure and function is dependent on the net effect of these forces (for example, protein folding), therefore it follows that an increase in chaotropic solutes precipitated by an implant in a biological system will denature macromolecules, reduce enzymatic activity and induce stress on cells. In particular, tertiary protein folding is dependent on hydrophobic forces from amino acids throughout the sequence of proteins. Chaotropic solutes decrease the net hydrophobic effect of hydrophobic regions because of a disordering of water molecules adjacent to the protein. This solubilizes the hydrophobic region in the solution, thereby denaturing the protein. This is also directly applicable to the hydrophobic region in lipid bilayers; if a critical concentration of a chaotropic solute is reached (in the hydrophobic region of the bilayer) then membrane integrity will be compromised, and the cell (tissue layer) will lyse.

Many implants that degrade into acids form chaotropic salts that are water soluble and exert chaotropic effects via a variety of mechanisms. Whereas chaotropic compounds such as hydroxyl compounds, for example polyethylene glycol, interfere with noncovalent intramolecular forces, salts can have chaotropic properties by shielding charges and preventing the stabilization of salt bridges. Hydrogen bonding is stronger in nonpolar media, so salts, which increase the chemical polarity of the solvent, can also destabilize hydrogen bonding. The loss of hydrogen bonding disassociates the delimiters of tissue layers, promoting translayer bridge formation. In terms of intersurface dynamics, the formation of adhesions is promoted due to insufficient water molecules to effectively solvate the ions resulting from surgical tissue disruption. This can result in iondipole interactions between the salts and hydrogen bonding species which are more favorable than normal hydrogen bonds, which accordingly promote bridging between tissue layers over promotion of tissue layer boundaries.

Accordingly, it is important that an antiadhesion prosthetic that is absorbable not contribute to a chaotropic effect.

Granted much of the denaturation due to surgical intervention is due to disruption of tissue layers, cell death and perturbation of the ionic and hydrophobic equilibrium established in living tissue. Thus, a barrier material should be chemically neutral and reestablish the structural aspects of the tissue perturbed by surgical intervention. Since this intervention is intended to be temporary, then the elimination of the barrier material itself must not be chaotropic. This is where most absorbable materials fail. In cases where an implant is intended to disappear to minimize site colonization by endogenous bacteria, and the implant serves a mechanical function, then such chaotropic effects may be acceptable in a risk/benefit analysis. But where a material is specifically implanted for the purpose of reestablishing normal tissue structure, such chemotropic effects may not be ignored.

Additional background information includes the following:

U.S. Pat. No. 6,312,725 discloses compositions suited for use in a variety of tissue related applications when rapid adhesion to the tissue and gel formation is desired U.S. Pat. No. 6,399,700 discloses comb copolymers comprising hydrophobic polymer backbones and hydrophilic noncell binding side chains which can be endcapped with cell-signaling ligands that guide cellular response.

U.S. Pat. No. 6,413,539 discloses hydrogelforming, self-solvating, absorbable polyester copolymers capable of selective, segmental association into compliant hydrogels upon contacting an aqueous environment.

U.S. Pat. No. 6,465,513 discloses compounds useful in the treatment of inflammatory diseases.

U.S. Pat. No. 6,486,140 discloses the use of chitosan and a polysaccharide immobilized thereto selected from heparin, heparin sulphate and dextran sulphate for the manufacture of an agent capable of preventing or substantially reducing undesirable adhesion of damaged tissue with adjacent or surrounding tissues in connection with wound healing; and a process for the use of such agent.

U.S. Pat. No. 6,486,285 discloses a water-swellable polymer gel prepared by reacting an ester of a carboxyl group containing polysaccharide with a compound having at least two .alpha.amino groups, which is derived from a natural amino acid, and a foamed article thereof.

U.S. Pat. No. 6,514,522 discloses polysaccharide polymers, for example, chitosanarabinogalactan and polysaccharide amine polymers are disclosed. The polymers can be used to prevent wound adhesion, to provide scaffolds for tissue transplantation and carriers for cell culture.

U.S. Pat. No. 6,642,363 discloses materials which contain polysaccharide chains, particularly alginate or modified alginate chains. The polysaccharide chains may be included as side chains or auxiliary chains from a backbone polymer chain, which may also be a polysaccharide. Further, the polysaccharide chains may be crosslinked between side chains, auxiliary chains and/or backbone chains.

U.S. Pat. No. 6,903,199 discloses waterinsoluble, crosslinked amide derivatives of hyaluronic acid and manufacturing method thereof, where the amide derivatives of hyaluronic acid are characterized by crosslinking, of polymer or oligomer having two or more amine groups, with hyaluronic acid or its hyaluronate salts through amidation reaction.

U.S. Pat. No. 6,923,961 discloses carboxypolysaccharides including carboxymethyl cellulose and their derivatives are provided that can be made into sponges, gels, membranes, particulates and other forms, for a variety of antiadhesion, antithrombogenic, drug delivery and/or hemostatic applications during surgery and pharmacological therapeutics.

U.S. Pat. No. 7,026,284 discloses a polyphenol useful as a gene complex, cell adhesion inhibitor or immune tolerogen. The polyphenol of forming the agent is selected from catechin group consisting of epigallocatechingallate, tannic acids, or proantodianisidine, a protein of the protein complex is selected from proteins consisting of animal proteins composed of polypeptide chain of peptidecombined amino acids, vegetative proteins, nucleus proteins, glycogen proteins, lipoproteins and metal proteins, the gene complex comprises by compositing genes by polyphenol catechins in order to introduce genes to cells of animals or human bodies, a cell composed of the cell adhesion inhibitor is selected from cells consisting of an animal cell including a stem cell, skin cell, mucosa cell, hepatocyte, islet cell, neural cell, cartilage cell, endothelial cell, or epidermal cell.

U.S. Pat. No. 7,265,098 discloses methods for delivering bioadhesive, bioresorbable, antiadhesion compositions. Antiadhesion compositions can be made of intermacromolecular complexes of carboxylcontaining polysaccharides, polyethers, polyacids, polyalkylene oxides, multivalent cations and/or polycations.

U.S. Pat. No. 7,316,845 discloses compositions for coating biological and nonbiological surfaces, which minimize or prevent cell-cell contact and tissue adhesion, and methods of preparation and use thereof, are disclosed. Embodiments include polyethylene glycol/polylysine block or comb-type copolymers with high molecular weight PLL (greater than 1000, more preferably greater than 100,000); PEG/PLL copolymers in which the PLL is a dendrimer which is attached to one end of the PEG; and multilayer compositions including alternating layers of polycationic and polyanionic materials.

U.S. Pat. No. 7,569,643 discloses novel polymeric compositions based upon $A_n(BCB)A_n$ polyester/polyether multiblocks.

U.S. Pat. No. 7,879,356 discloses novel bioabsorbable polymeric compositions based upon AB polyester polyether or related diblocks and triblocks.

U.S. Pat. No. 7,883,694 discloses crosslinked polymer compositions that include a first synthetic polymer containing multiple nucleophilic groups covalently bound to a second synthetic polymer containing multiple electrophilic groups. The first synthetic polymer is preferably a synthetic polypeptide or a polyethylene glycol that has been modified to contain multiple nucleophilic groups, such as primary amino ($NH_2$) or thiol (SH) groups. The second synthetic polymer may be a hydrophilic or hydrophobic synthetic polymer, which contains or has been derivatized to contain, two or more electrophilic groups, such as succinimidyl groups.

U.S. Pat. No. 7,994,116 discloses to a method for prevention or reduction of scar tissue and/or adhesion formation wherein a therapeutically effective amount of a substance that inhibits a proinflammatory cytokine.

U.S. Pat. No. 8,003,782 discloses that a pharmaceutical composition containing complex carbohydrates with or without natural or synthetic essential oils can work effectively as a topical, oral or mucosal pharmaceutical composition.

U.S. Pat. No. 8,048,444 discloses an implant introduced into a surgical site of a patient to prevent postsurgical adhesions.

U.S. Pub. No. 20090208589 discloses new biopolymers which mimic the properties of natural polysaccharides found in vivo. The inventive polysaccharides can be used as viscosupplements, viscoelastics, tissue space fillers, and/or antiadhesive agents.

U.S. Pub. No. 20100160960 discloses hydrogel tissue adhesive is formed by reacting an oxidized polysaccharide with a waterdispersible, multiarm amine in the presence of a polyol additive, which retards the degradation of the hydrogel.

U.S. Pub. No. 20110166089 discloses provide a solution for tissue adhesion prevention and a method for tissue adhesion prevention that are applicable to general surgery and in which covering condition during surgery is stable and convenient. The invention is the solution for tissue adhesion prevention of which the active ingredient is trehalose.

U.S. Pub. No. 20110237542 discloses to a composition for preventing tissue adhesion which comprises a biocompatible hyaluronic acid and a polymer compound. More specifically, the invention is a composition containing hyaluronic acid which has not been modified by a chemical crosslinking agent.

U.S. Pub. No. 20110243883 discloses provides branched polymers which can be used as lubricants or shock absorbers in vivo. For example, the inventive polymers can be used as viscosupplements, viscoelastics, tissue space fillers, and/or antiadhesive agents.

BRIEF SUMMARY OF THE INVENTION

In view of the limitations inherent in the above cited patents and status of the art, it is an object of the present invention to provide a gel optionally comprising at least one solid phase and optionally comprising a biologically active aspect. The bioactive aspect can be geometrical, chemical, or mechanical.

Yet another object of the present invention is to provide a gel polymer optionally terminated with a biologically active agent.

A further object of the present invention, is to provide a gel polymer capable of the controlled release or presentation at an implant surface of a biologically active agent/drug for modulating cellular events, such as, wound healing and tissue regeneration.

A further object of the present invention, is to provide a gel polymer capable of the controlled release or presentation at an implant surface of a biologically active agent/drug for therapeutic treatment of diseases.

A further object of the present invention, is to provide a gel polymer which is capable of being extruded onto or injected into living tissue for providing a protective barrier with or without an anti-inflammatory agent or an agent which inhibits fibrotic tissue production for treating conditions, such as, postsurgical adhesion.

A further object of the present invention, is to provide a gel polymer which is capable of being extruded onto or injected into living tissue for providing a protective barrier with or without a wound healing agent or an agent which promotes vascularization for treating conditions, such as, repairing a soft tissue defect.

A further object of the present invention, is to provide a gel polymer which is capable of being extruded onto or injected into living tissue for providing a first protective barrier aspect and a second tissue scaffold aspect, wherein each aspect comprises a separate phase.

A further object of this invention is to provide a gel polymer for delivering a botanical extract possessing anti-inflammatory or wound healing properties, for example extracts derived from the genus *Boswellia*.

A further object of the present invention is to provide a gel polymer comprising distinct phases, each of the phases designed to a specific absorption rate to achieve a specific functional aspect.

A further object of the present invention is to provide a gel polymer comprising distinct phases wherein the gel phase is tissue adhesive to achieve localization and prevent migration of the gel after implantation at an intended site. A further object of the present invention, is to provide a gel polymer comprising distinct phases wherein the gel phase is lubricious, and minimizes the irritation associated between adjacent layers of tissue created during a surgical operation that involves tissue dissection.

A further object of the present invention is to provide a gel polymer comprising distinct phases wherein the different phases are temporarily linked such that as the ionic linker is solvated in vivo, the linking strength is diminished.

A further object of the present invention is to provide a gel polymer comprising distinct phases wherein the solid phase binds the gel phase, such that the gel phase is not free to spread or swell without limit.

A further object of the present invention is to provide a gel polymer comprising distinct phases wherein the solid phase and gel phase possess shape memory and the shape achieved during manufacturing and formation of the gel system is a low energy state of the gel system.

A further object of the present invention is to provide a gel polymer comprising distinct phases wherein the combination of phases This present disclosure generally addresses methods of treating tissue defects and modulating cell to cell interactions and tissue to tissue interactions by administration of a polymeric gel material incorporating nongel phases which optionally may contain bioactive molecules to facilitate the repair of a tissue surface.

The present disclosure further provides biomedical and pharmaceutical applications of absorbable or biodegradable multiphasic hydrogels, where optionally one or more phases are not absorbable in situ. More particularly, the present invention relates to multiphasic systems of hydrogels comprising gel and non-gel phases, wherein these phases may be coupled mechanically, hydrophobically, by metal ions, or by covalent bonds. The disclosure further provides methods of using multiphasic gels in humans for providing: a) a protective barrier to prevent postsurgical adhesion, b) a carrier of tissue scaffolding, c) a sealant for isolating layers of tissue chemically, d) a lubricious aspect to ameliorate or reduce tissue inflammation, e) an ordering aspect to reduce the entropy of the healing process, and f) a controlled composition for delivery of biologically active agents for modulating cellular signaling such as wound healing and tissue regeneration or therapeutic treatment of diseases such as cancer and infection.

The disclosure relates to materials that contain polysaccharide chains or polyester chains, particularly hyaluronan or galactomannan chains, but includes modified cellulose, alginate, polylactic acid, polyurethane, and ethylene or propylene moieties.

The polysaccharide, particularly hyaluronan or galactomannan chains may be included as side chains or auxiliary chains linking phases, and in particular gel and solid phases.

The gel phase backbone is typically an ether, containing ethylene and/or propylene structure. For example, a backbone can comprise a poloxamer. In other embodiments, the backbone may also be a polysaccharide, such as hyaluronan associated with galactomannan.

Hyaluronan is a polymer of disaccharides, themselves composed of Dglucuronic acid and D-Nacetylglucosamine, linked via alternating beta1,4 and beta1,3 glycosidic bonds. Galactomannans are polysaccharides consisting of a mannose backbone with galactose side groups (more specifically, a (14) linked betaDmannopyranose backbone with branch points from the 6positions linked to alphaDgalactose. Any combination of these subunits comprising hyaluronan and galactomannan are contemplated by the present disclosure.

Further, the polysaccharide chains may be crosslinked between side chains, auxiliary chains and/or backbone chains. These materials are advantageously modified by covalent bonding thereto of biologically active molecules for cell adhesion signaling or other cellular messaging.

This disclosure relates also to derivatized carboxypolysaccharides (CPS). Specifically, the disclosure relates to derivatized carboxypolysaccharides and uses in manufacturing gels incorporating polyethylene oxide (PEO) or polypropylene oxide (PPO) for drug delivery and for antiadhesion preparations. More specifically, this invention relates to antiadhesion and healing compositions comprising composites of biofunctionalized CPS, PEO and PPO.

One embodiment is directed to a multiphasic gel, wherein the gel phase comprises a poloxamer polymer backbone to which is linked polysaccharide groups, particularly of hyaluronan or galactomannan. The polysaccharide groups are present as side chains or alternating with the poloxamer in a chain configuration. The chains may be polymerized into rings, thus eliminating any endgroups. The gel polymers provide synthetically modified polysaccharides exhibiting controllable mechanical and charge distribution properties to which an organic moiety may be attached.

Further, the disclosure is directed to processes for preparing such polymers including an organic moiety and to the use of such polymers, for example, as cell transplantation matrices, preformed hydrogels for cell transplantation, nondegradable matrices for immunoisolated cell transplantation, vehicles for drug delivery, wound dressings and antiadhesion prosthetics.

Another embodiment is directed to polysaccharides, particularly hyaluronan, which are modified by being crosslinked with an organic bioactive moiety. The hyaluronan may further be modified by covalent bonding thereto of a biologically active molecule for cell adhesion, cell repulsion, or other cellular interaction. Crosslinking of the hyaluronan with a poloxamer can particularly provide polysaccharide/polyether materials with controlled mechanical properties and shape memory properties which greatly expand their range of use.

In many applications, such as tissue engineering, size and shape of the matrix is of importance. The modification of the crosslinked polysaccharides with the biologically active molecules can provide a further three dimensional environment. Then finally the addition of a solid phase, with a particular geometry tuned to the healing process, provides essentially a four-dimensional environment. For example, a gel tends to take the shape of the vessel which contains it, but a system of solid torus, polymerized into the gel matrix so as to form a chainmaillike configuration, can internally constrain a gel dimensionally to prevent gel thinning, clumping, or partitioning.

Another embodiment is directed to modified polysaccharides, such as polymers containing a poloxamer backbone with the above described side chain hyaluronan or crosslinked hyaluronan, modified by covalent bonding thereto of a biologically active molecule for mitigation of cell adhesion or other cellular interaction, which is particularly advantageous for maintenance, viability and directed expression of desirable patterns of gene expression. For example, a terminal group that stimulates nitric oxide production and promotes angiogenesis. Alternatively, a terminal group that comprises a constituent of a botanical extract with healing or antiaging properties.

In particular, a biofunctional molecules optionally could be those obtained from various extracts and purification of *Boswellia* genus botanicals. More particularly, the extracts have a polycyclic structure with one or more pendant hydroxyl groups. These biofunctional molecules are covalently bonded, using the hydroxyl group, to join a polymeric backbone or side chain to the biofunctional molecules. Preferably, the biofunctional molecule is chiral. The chirality can be due to an odd number of cyclic structures, or an asymmetric terminal chain. The biofunctional molecules may include synthetic analogues of naturally occurring structures.

The present compositions are preferably advantageously used, for example, in the reduction or prevention of adhesion formation subsequent to medical procedures such as surgery and as lubricants and sealants. In addition, compositions according to the present invention may be used as coatings and transient barriers in the body, for materials which control the release of bioactive agents in the body (drug delivery applications), for wound and burn dressings and for producing biodegradable and nonbiodegradable articles, among numerous others.

The present disclosure includes a multiphasic structure; each of the phases may be directed to a different cellular response or purpose. In particular, a gel aspect may provide an antiadhesive functionality which resorbs in the body. Secondly, a solid phase can provide a tissue scaffold aspect, which aids in the ordering of tissue repair and rejuvenation, such that metabolic functionality is encouraged over fibrosis and walling off of the repair site.

Lastly, the present disclosure incorporates a solid phase that provides a lubricious aspect unattainable with a homogenous gel phase. The solid phase acts as a mechanical analogue to ball bearings, and the gel phase acts as a lubricant. In combination, freshly excised tissue surfaces are both sealed and hydrated while the solid phase prevents tissue bridging by contact and a dimensional rolling aspect, which serves to separate as well as facilitate differential motion, which is common between dissected layers of tissue.

The chemical structures and methods of the disclosure concern gels, more particularly hydrogels, comprising hydrophilic blocks, hydrophobic blocks and biofunctional moiety. The hydrogels of the present invention are intended for implantation in a mammalian body and may be absorbable or alternatively relatively persistent. These hydrogels are characterized by possessing at least two distinct phases, be they liquid, solid, gas, or distinctly a gel.

A hydrogel is a polymeric material with a high tendency for water absorption and/or association, which maintains mechanical integrity through physical crosslinks or polymeric entanglements which are reversible or degradable in vivo. The hydrophobic blocks may be absorbable polyester chain blocks, polyoxypropylene blocks, urethane segments and botanical extract molecules. Of particular interest are cyclic lactones, for example glycolide, llactide, dllactide, epsilon.caprolactone, and p dioxanone. With respect to botanical extracts, polycyclic structures are of particular interest, for example boswellic acid derived from *Boswellia*. Examples include, boswellic acids, tirucalic acids, thujenes, champhenes, and the like, or their synthetic analogs.

The hydrophilic blocks may be polyoxyethylene blocks, polysaccharides, or derivatives hereof. The length of the hydrophilic block and its weight fractions can be varied to modulate the in situ volume equilibrium of the gel, its modulus, its water content, diffusivity of bioactive drug through it, its adhesiveness to surrounding tissue, and bioabsorbability.

The polymers constructed from these constituents are typically long chains with multiple pendant end groups, commonly referred to as comb or brushtype copolymers that elicit controlled cellular response. Examples of brush type polymers are hyaluronan and galactomannan. The backbone or chain portion of the polymer can be biodegradable or nonbiodegradable, depending on the intended application. Biodegradable backbones are preferred for most tissue engineering, drug delivery and wound healing device applications, while nonbiodegradable backbones are desirable for permanent implant applications. A portion of the side chains can be endcapped with cellsignaling polycyclic structures functionalized with ligands to control the degree of cell adhesion and tissue healing. The cellsignaling can be elicited at a phasic polymer surface or released into the surrounding tissue through degradation of a portion of the polymer.

In the preferred embodiment, the overall comb copolymer should have a molecular weight sufficiently high as to confer good mechanical properties to the polymer in the hydrated state through chain entanglement. That is, its molecular weight should be above the entanglement molecular weight, as defined by one of ordinary skill in the art.

The overall molecular weight of the comb copolymer should thus be above about 30,000 Daltons, more preferably above 100,000 Daltons, and more preferably still above 1 million Daltons. The side chains are preferably hydrophilic and degradable, and the polymer backbone contains a multiplicity of hydrophilic, degradable blocks. The density of the hydrophilic side chains along the backbone of the polymers depends on the length of the side chains and the water solubility characteristics of the final polymer. The total percentage by weight of the hydrophilic side chains is between 10 and 50 percent of the total copolymer composition, preferably around 30 percent by weight. Preferably, the hydrophilic side chains associate with water and form a hydrated layer which repels proteins and hence resists cellular adhesion.

The side chains of the comb polymer can be endcapped with cellsignaling

Molecules modified by chemical ligands in order to elicit controlled cell responses. Ligands capable of bonding to hydroxyl groups, for example diisocyanates, can be covalently attached to the hydroxyls of biofunctional molecules and in turn attached to the hydroxyl groups of the polymer side chains.

A defined fraction of biofunctionalized side chains can be obtained by using appropriate stoichiometric control during the coupling of the ligands to the polymers, by protecting the endgroups on those side chains which are not to be endcapped with the biofunctional molecule, or by combinations of these approaches. Generally, the ligands are attached to the biofunctional molecule first, which then enables the biofunctional molecules to link to the polymer side chains without leaving exposed ligands which may promote protein attachment and subsequently adhesions.

Typically the number of phases in a gel system are two, comprising a gel fraction and a solid fraction. However, the number of phases is unlimited, and may include phases of different degradation rates. While the gel aspects of the present invention possess a characteristic viscosity, that viscosity can change with temperature and pH. Typically, the gel systems of the present invention are nonNewtonian, and more typically are thixotropic. Alternatively, the gels can be constituted to be antithixotropic, as in starch suspensions.

In the case of solid particles suspended, polymerized, or encapsulated within a gel phase, the particulate fraction is typically longer lasting and structural. In a structural aspect, tori are of particular utility since they possess high symmetry and can act as pivots in a gel system. Also importantly, they can act as chainmail, linking gel domains while providing both translational and rotational freedom. They are particularly useful when the gel is surface polymerized to the solid.

Alternatively, the solid aspect can be a sphere, wherein there is no interpenetration of he gel through the solid, and all the coupling, if any, is surface mediated. In this configuration, the spheres act as stress reliever, allowing for rotational freedom in a gel where stresses may develop differentially between surfaces.

Additionally, the solid surfaces may be polyhedral, wherein at a certain compressional density or thinning as a result of forces between adjacent tissue layers, the solid particle lock together, providing a step function resistant to further thinning or mobilization of the gel phase.

In refined aspects, any of the above basic geometric considerations can be further enhanced by texturing a solid phase surface. For example, several micron sized solids can be texturized with nanometer scale structure. Such surface nanoscale structures could be in the shape protrusions. Examples of protrusions are pyramids, hooks, bumps, or undulations. Alternatively, the surface features could be in the shape of indentations. Examples of indentations include recessions of every geometric shape, in particular cylindrical depressions, conical depressions and the like. Clearly, a hybrid of protrusions and depressions are considered. In particular, a reference plane may be established, wherein there are alternating depressions and protrusions separated by a flat planar surface of relatively small total surface area.

Regarding tori and related structures, structures of the present invention may be of any genus. Long strands of many tori contacting at an edge may be considered, as well as closed forms such as loops and even three dimensional forms such as icosahedrons, and the like. Any platonic solid is contemplated.

The solid phase may be composite, that is, coated or comprising layers. The coating may facilitate a short term bonding between solid and gel phases. The surface may provide an initial interaction with the gel phase that dissipates by absorption. The surface may achieve a mechanical aspect that upon absorption transitions to a tissue reactive aspect. In particular, a monofilament torus may degrade into a multifilament torus, wherein once the outer coating is resorbed the loosely toroid multifilamentous structure facilitates tissue association. The coating itself may comprise yet smaller solid phase structures that absorb or disperse within the gel component. These smaller dimensional structure may carry a chemically active moiety. The solid phase may be principally responsible for an adhesive aspect, and this aspect may be modified by time. In particular, the particles may be first adhesive and later antiadhesive.

The particles may be structure such that they migrate toward high energy surfaces, for example the interface between the gel system and a tissue surface. It may be advantageous that the solid phase and the gel phase be constituted of essentially the same chemical constituents, and only differing in the crosslink density or degree of association with water.

Accordingly, aspects such as resorption time, viscosity, hydrophobicity, etc. can be modified in a layered approach, and by the selection of multiple phasic elements. The total gel system of the present invention can be designed for resorption times on the order of hours to several months. The gel system of the present invention is preferably resorbed in an amorphous state, in particular crystalline states are explicitly to be avoided. For example, design considerations such as considerations of chirality are preferably employed, as known in the art, to avoid a fracture degradation pathway. Whenever possible, the formation of hard particulate matter, except when intended, is to be avoided. For example, it is preferred that the degradation products of a gel system do not form numerous, spherical, highly fibrotic centers. And in particular, it is especially to be avoided, the formation of said centers wherein the implant matter is sequestered from normal degradation processes, and persist for an extended period. Such centers have been associated with late stage endogenous infection.

In one embodiment, the disclosure provides a backbone of polyoxyethylene, polyoxypropylene, or combinations of these in chain form with multiple hydroxyl groups to which are covalently attached side chains of polysaccharides. It is not necessary that the polysaccharides exhibit the gelling behavior of alginates, since the backbone can alternatively form a hydrogel. In this case the main function of the polysaccharide would be to control the degradation rate, provide a tissue adhesive functionality and modify the hydrophobicity of biofunctional end groups.

Another embodiment provides a polymeric backbone section to which is bonded a side chain, preferably multiple side chains, of polymerized, optionally modified hyaluronan and galactomannan. The modified polysaccharides preferably maintain the mild gelling behavior of conventional hyaluronan sulfate. The linkage between the polymeric backbone section and the side chains may be provided by difunctional or multifunctional linker compounds, for example diisocyanates, or by groups incorporated within the polymeric backbone section reactive with the polysaccharide units or by groups on the polysaccharide units or derivatives thereof reactive with groups on the polymeric backbone section. The polymers may advantageously further comprise biologically active molecules bonded to the side chains, particularly preferably bonded through the hydroxyl groups on hyaluronan and galactomannan.

In a particularly preferred embodiment, the side chains are hyaluronan, the biologically active molecules exhibit cell antiadhesion properties and the polymers provide a mucoadhesivity for localizing the hydrogel in vivo without forming tissue adhesions.

In a yet more preferred embodiment, the side chains are hyaluronan, the biologically active molecules are of two types, some of which exhibit cell antiadhesion properties and others exhibit angiogenic properties, and the polymers provide a mucoadhesivity for localizing the hydrogel in vivo to repair a wound site and protect the healing wound site from tissue adhesions.

When a linker group or ligand is used, such linker groups may be selected from any divalent moieties which are compatible with the ultimate use of the polymer and which provide for covalent bonding between the polymeric backbone section and the polysaccharide side chains and additionally any biofunctional end groups. Additionally, the liner groups may link to the other phasic fractions, in particular, a solid phase of absorbable polyurethane.

When polysaccharides are used, it is conventional for the polysaccharide to be bonded through a carboxylate group. In this case, the linker group may be selected to significantly affect the biodegradability of the polymer depending upon the extent of hydrolyzability of groups in the linker chain. For example, amino acid linkers are frequently used due to the controllability of the degradation interval. For example, amino acid linker groups, such as glycine, will provide ester linkages which are readily hydrolyzable and, thus, facilitate degradation of the polymer in an aqueous environment, whereas, amino alcohols provide an ether linkage which is significantly less degradable. Amino aldehydes are also useful linker groups. The substituent groups on the amino acids will also affect the rate of degradability of the linkage.

The linker group may also be varied in chain length depending upon the desired properties. Linkages providing, for example, from 10 to 20 atoms between the backbone and side chain, are typical, although longer linkage chains are possible. Additionally, the linker may be branched to provide for clustering of multiple side chains. These structures are typically referred to as dendritic in structure because they may provide a multiplicity of branching points.

The polymeric backbone section, linkages, side chains and biofunctional end groups may be provided in a number of hydrophilic and hydrophobic configurations which will largely determine the stability of the resulting hydrogel. The polymeric backbone itself may comprise alternating hydrophobic and hydrophilic blocks. Since the biofunctional endgroups are typically hydrophobic, it is generally useful to modify their hydrophobicity by attaching them to hydrophilic side chains.

DETAILED DESCRIPTION OF THE INVENTION

Figure 1:
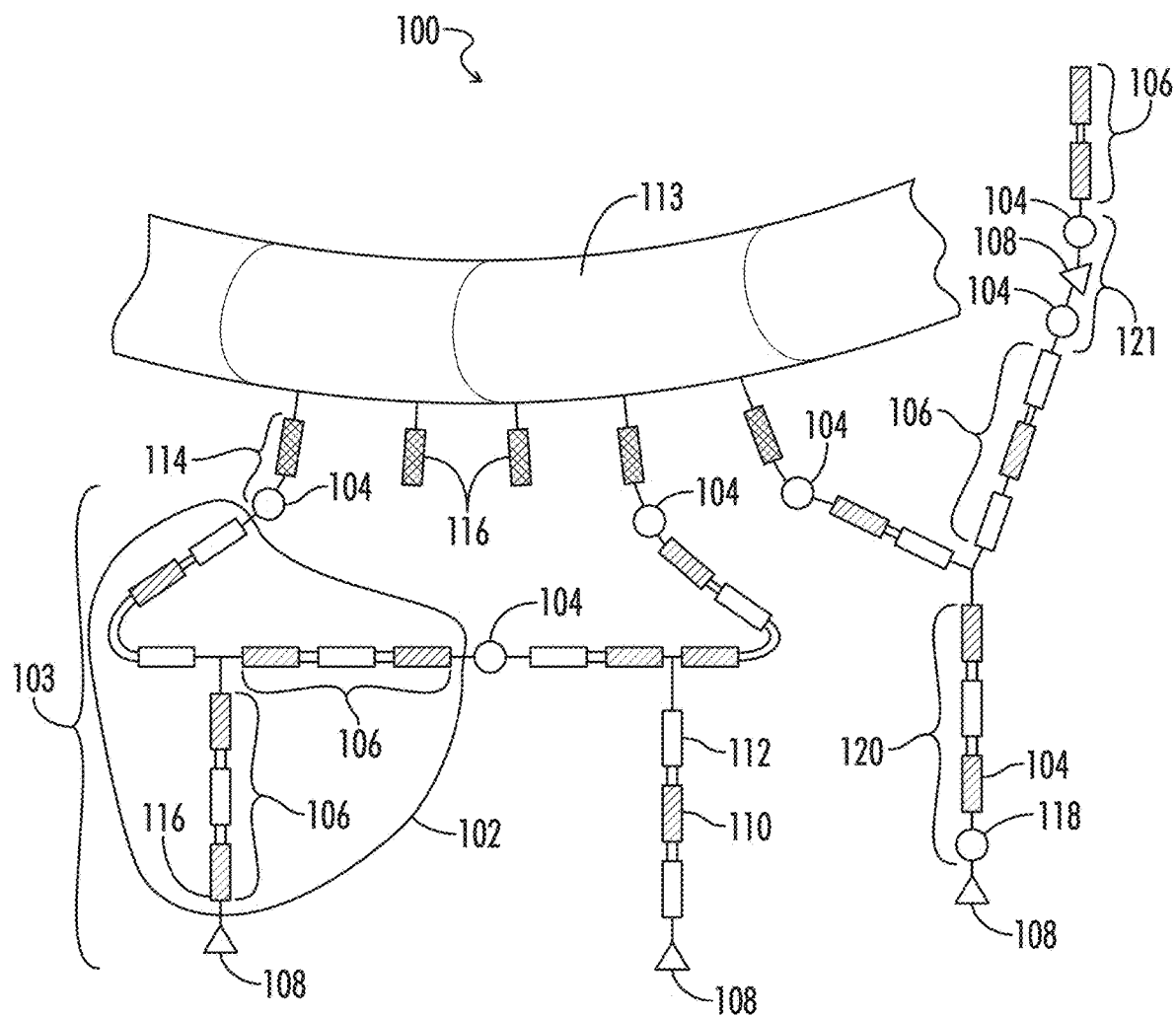
FIG. 1 depicts a multiphase gel polymer system 100 of the present disclosure.

Homogenous adhesion barrier gels should not admit tissue in-growth initially upon implantation, otherwise their efficacy relating to establishing separate tissue layers would be obviated. Thus, as the homogenous gel portion resorbs, there may be need for a tissue scaffold, in particular a tissue scaffold that has an appreciably longer duration than the gel barrier, such that when the gel has been resorbed, or nearly so, the second scaffold aspect come increasingly more dominant.

For example, the gel in the initial time course may be highly absorbable, and correspondingly chaotropic, due to release of byproducts that disrupt local equilibrium. However, at this early stage, when tissues are far from normal equilibrium states, a barrier layer may be more important than chaotropic considerations. However, as the surgical intervention aspect is resolved, it is desirable that the anti-adhesion barrier not contribute to chronic inflammation and any aspect of entropy increase. Furthermore, it is advantageous that the gel aspect transition to a tissue scaffold aspect, wherein order is presented or reestablished to the tissue surface, wherein normal barrier layers may be stabilized or promoted.

Naturally, this consideration calls for a two stage repair, in which first a barrier aspect is temporarily presented and subsequently replaced by an ordering and chemically neutral aspect. It should be appreciated that by chemically neutral we do not mean that the second ordering aspect is strictly permanent, but rather that its degradation byproducts are either sufficiently chemically neutral or that the degradation period sufficiently long, such that normal tissue structures are reestablished without interlayer bridging.

Compounds useful in the present disclosure are generally classified as complex carbohydrates. For purposes of this invention complex carbohydrates are defined as any polymer comprising more than two sugar moieties including such classes of compounds as polysaccharides and oligosaccharides. Polysaccharides include mucopolysaccharides and mannans whereas oligosaccharides comprise branched polysaccharides such as sialylated sugars including milk sugars.

Mucopolysaccharides are glycosaminoglycans, which can be obtained from numerous sources (e.g. rooster combs, trachea, umbilical cords, skin, articular fluids and certain bacteria such as Streptococci). Most glycosaminoglycans (hyaluronic acid, chondroitin sulfates A, B, and C, heparin sulfate, heparin, keratan sulfate, dermatan sulfate, etc.) are composed of repeating sugars such as nacetylglucosamine glucuronic acid and nacetyl galactosamine (these are known as nonsulfated glycosaminoglycans). If such glycosaminoglycans contain sulfur groups they are known as sulfated glycosaminoglycans. All of these can be combined with other polysaccharides or with alkane groups.

The present application combines bioactive groups with biocompatible groups to address wound healing through a positive physiological reaction that may restore anatomy and function of various tissues after trauma without inflammatory interference. The trauma may be accidental, the result of surgical intervention or the effect of a disease or genetic condition. The ideal end result of wound healing is restoration of tissues morphology. Restoration of tissue morphology requires directing a functional aspect as well as reducing high entropy responses, such as scar formation.

One prevalent part of the wound healing process is to form connective tissues or scar tissue that may support the healing tissues during wound healing and regeneration. However, in many cases during wound healing, the newly formed connective tissues (scar tissue) may interfere negatively with the normal function of the tissue intended to be healed. In general, such tissue responses are characterized by a high degree of disorder, and characteristically lack a metabolic component, wherein the tissue formed is primarily avascular. Wound healing, with the formation of connective tissues may also induce adhesions that may induce pathological conditions. For example, scar tissue may induce cosmetically undesirable results such as cheloid formation. Examples of adhesions and scarring may be found virtually in any organ or tissue undergoing wound healing after trauma or surgery. Following abdominal surgery and following gynecological surgery it is not uncommon that the surgical procedure may induce adhesions that may both make later surgery more difficult and induce pathological conditions such as ileus.

In spinal surgery it is common to have a situation with a dense scar formation called epidural fibrosis. This may in certain cases induce significant difficulties for repeated surgery and can induce compression of the adjacent nerve tissue. In other organs excessive wound healing may induce unwanted fixation of tissues and structures that may reduce function and induce pathological conditions.

In general, a method for controlling wound healing, particularly the reduction of cellular random scar tissue and adhesions, would be of a great value in most cases of posttraumatic or postsurgical wound healing. Thus, it is insufficient to merely reduce the stimulus to the formation of scar and adhesions by blocking such formation or providing an ameliorative coating, but also a repair of the surgically corrected defect must be facilitated or directed which includes a metabolic aspect such that repeated resorption and modification of the repair site is reduced.

Intercellular adhesion mediated by VLA4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. A polymer that mitigates fibrosis, while promoting endothelial and leukocyte infiltration, can be promotional to wound healing and antimicrobial. Surprising, it has been discovered that a single phase antiadhesion substance can be insufficient in several aspects. In particular, an aspect that is distinct from the mechanical characteristics of a gel barrier can serve as a structural impetus, encouraging avenues of repair not realized in homogenous materials.

In intraorgan systems, tissue damage occurs that elicits an adhesion mechanism that results in migration or activation of leukocytes that can be damaging. For example, the initial insult following myocardial ischemia to heart tissue is complicated by leukocyte entry to the injured tissue causing still further insult. Inflammatory conditions mediated by adhesion mechanisms are almost always deleterious, for example, asthma, Alzheimer's disease, atherosclerosis, AIDS dementia, diabetes, inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocytemediated lung injury such as that which occurs in adult respiratory distress syndrome. Therefore, it is desirable to develop a hydrogel which combines a barrier aspect with a structural biofunctional aspect and optionally a chemical biofunctional aspect which also affects cellular adhesion and prevents clinically adverse tissue adhesions.

One difficulty associated with implantable hydrogel compositions is that optimizing the composition to relative to gel mechanical characteristics, in particular the absorbability may worsen tissue inflammation at the site of administration. A possible explanation for this effect is that highly reductive compositions are capable of promoting rapid leukocyte infiltration which may adversely affect tissue responses.

Accordingly, the hydrogel aspect of the present disclosure is hydrophilic and avoids the adverse events of polymers currently in use for biomedical applications which are generally hydrophobic. However, a relatively more hydrophobic component with a structural aspect, such as tori polymerized within a gel matrix, may provide a tissue regenerative response associated with the reformation of functional and metabolic tissue.

As defined herein, hydrophobic refers to a material that repels water and exhibits a static contact angle with water greater than 60 degrees at 20 degrees C., and has a water permeability less than 3×10 10 cm 3 (STP) cm/(cm 2 s Pa). Hydrophobicity can give rise to uncontrolled interactions between cells and adsorbed proteins at the surface of an implanted material, which can result in a chronic inflammatory response that can lead to failure of implants and even promote tumorigenicity. Therefore, it is advantageous to encapsulate such materials, even mildly hydrophobic materials, within a gel matrix which provides initial sequestration, until normal cellular responses are reestablished, and radical foreign body responses are minimized, and a normal regenerative function characterized by a low degree of entropy can be established.

On the other hand, for tissue healing applications, it is desirable that the polymeric material used to form a biodegradable scaffold for cells, promote cell adhesion, migration, growth and differentiation while providing adequate morphological stimulus; and without promoting an inflammatory response. Though commonly used synthetic scaffold materials such as polylactide, polyglycolide, etc., and copolymers thereof, have suitable mechanical, processing and biodegradation properties, their hydrophobic nature and acid byproducts leads to protein adsorption and denaturing of proteins attached to the material surface which elicits uncontrolled inflammatory response.

The present disclosure couples tissue directing materials with hydrophilic moieties to reduce protein adhesion to the implant during the first highly reactive phase, and additionally may contain a selective bioactive material which can down regulate inflammation and promote tissue migration into a tissue defect to heal the defect rather than promote aggressive cellular response to the implant. The ideal antiadhesive surface for many biomaterials applications resists protein adsorption while providing molecules with specific chemical signals to guide tissue regeneration, survival, growth, migration and differentiation in an adjacent tissue defect.

As used herein, the term "biomaterial" refers to a material used in a medical device intended to interact with a biological system. Such biomaterial with biofunctionality may be chemical in nature, or structural, wherein the shape promotes a desired cellular response. For example, a typical biomaterial is modified with polyethylene oxide, which has been studied in recent years for the reduction of protein adsorption at the surface of biomaterials. The objective of these surface modification schemes is the elimination of nonspecific interactions of cells with implant materials. Polyethers can be combined with hydrophobic biomaterials to shield the hydrophobic biomaterials from the foreign body response, and thus provide them to the body directly rather than through a fibrotic capsule. Reduction of a fibrotic capsule is paramount, since these capsules are avascular, and serve to sequester implants from normal protective functions of the body. Implants associated with thick capsules are also associate many years after implantation. Thus, the teachings of the present disclosure are instructive regarding absorbable implants as well as permanent implants.

Regarding the chemical aspect of biofunctionalization of an implant, activation-specific chemical signals can be relayed to cells at a surface through tethered ligands of cell surface receptors. These signals are presented in a localized manner at a controlled dose without diffusive loss. The mimicry of tethered ligands through the addition of bioactive moieties may provide more constant stimulation to cells by avoiding the downregulation present when soluble ligands are internalized by cells. Control over spatial distribution of ligands on surfaces may also be key to guiding cell behavior. Thus systems which will allow spatial control of local ligand density through multiphasic architectures, or the creation of clusters of ligands on select surfaces, in addition to providing control over the average surface density of ligands on said surfaces, are highly desirable. In the present invention these ligands may be associated with a chemical biofunctional moiety or with a structural biofunctional phase.

Additionally, molecules with dimeric adhesion receptors are particularly useful as ligands and include approximately ten known alpha chains paired with one of approximately six known beta chains, which are known to mediate a wide range of interactions between cells and extracellular matrix and control cell behaviors as diverse as migration, growth, and differentiation, providing a permissive environment for the action of growth factors. Thus, such molecules are particularly useful in facilitating a healing response, especially when deployed in a multiphasic system.

An important aspect of healing involves cross-communication between adhesion and growth factor receptors, and it is hypothesized that these factors work competitively at a site of wound healing. Therefore, by favoring growth factor expression over adhesion formation a wound may be repaired prior to significant adhesion formation, thus shutting down significantly or entirely the stimulus for adhesion formation. The favoring of growth factor expression can be achieved chemically as well as structurally. Therefore, a biofunctional geometry delivered in close proximity to adhesion and growth factor receptors in the focal healing complex can modulate the flow of both positive and negative regulatory signals between the two. In particular, a hierarchical hydrophobichydrophilic domain structured polymer endcapped with a biofunctional molecule can beneficially undergo morphological changes which are associated with the hydration of the hydrophilic domains and formation of pseudocrosslinks via the hydrophobic component of the system. Such polymeric structures form biocompatible gels in vivo with extended persistence by virtue of the pseudocrosslinks. Domain separation can be enhanced by the inclusion of multiphasic domains, with and without structural aspects.

Hydrophobichydrophilic polymer morphology has been reported to be responsible for enhanced biocompatibility and superior mechanical strength due to formation of two phase structure comprising hydrophilic and hydrophobic domains. Such domains are a generic feature of many polyurethane systems, where the two phase structure is commonly referred to as amorphous and crystalline segments. This molecular structure can be mimicked in a macroscopic way, by incorporating solid hydrophobic structural elements in a hydrophilic gel phase.

Hydrophobic-hydrophilic polymer morphology can be affected by temperature and pH, especially for extended and hydrated systems, and is responsible for thermoreversible gels. In order for these gels to maintain their shortterm structure in vivo, regardless of their longerterm biodegradability, involves covalent bonds between watersoluble and waterinsoluble blocks. Some of the gels of the present invention are responsive to temperature and pH changes. For example, those containing poloxamers will shrink in size in a base environment and expand in an acidic environment. Similarly, higher temperature tends to cause the gels of the present invention to contracts, whereas lower temperature causes them to become more diffuse. In some instances, a low enough temperature causes them to solubilize and lose their thixotropic aspect. These considerations can be important in conditioning gel systems for implantation, since typically a hysteresis is associated with certain pH and thermal modifications, and some of these modifications can be considered irreversible below a certain energy threshold. Alternatively, such reversible modifications can be useful in manufacturing aspects in terms of purification, removal of residual monomeric components, and the preparation of gel precursors suitable for shelflife stability. In this later aspect, ionic constituents, such as salts, can achieve a similar effect.

In the case where the hydrophilic blocks and hydrophobic blocks are a mixture or blend and not polymerized together, the desired structural aspects are not achieved since the hydrophilic component rapidly disperses in tissue. Polymers comprising covalently bonded hydrophilic and hydrophobic domains exhibit a hydration dehydration equilibrium which can be altered by changes in temperature or pH. The equilibrium structures are characteristic of hydrogels. Thus, hydrogels of the present invention, in the absence of hydrophobic/hydrophilic covalent bonding, the hydrophilic blocks undergo intermolecular segmental mixing with the neighboring hydrophobic blocks to produce a viscous liquid. With hydrophobic/hydrophilic covalent bonding, competition between the water as an extrinsic solvent and the hydrophilic block forces the hydration of the hydrophobic block, and results in aggregation or association of the hydrophobic blocks to establish pseudocrosslinks which maintain a 3-dimensional integrity.

Three-dimensional stability can also be achieved by the use of metal ionic crosslinks, as is common in the preparation of alginates, and similar polysaccharides. The mechanism of gel formation for in vivo administration is associated with orientation of the hydrophobic blocks toward the exterior of the gel and the interface with the adjoining tissues can be used to establish an adhesive joint, which prevents gel migration from target site and sustains its intended efficacy. In some cases, a mucoadhesive functionality is desirable and achieved with most polysaccharide copolymerizations. Additionally, this effect can be enhanced by the insertion of a biofunctional structural form which is relatively more hydrophobic than the remaining gel portion of a polymeric chain of hydrophobic and hydrophilic blocks. Thus, the biofunctional moiety is presented preferentially at the phase discontinuities within the hydrogel and is predisposed to segmentation within the tissue.

Chemical bonding between phasic components can be carried out by a chemical reaction, e.g. gelation with a polyfunctional reagent; crosslinking using a coordinate bond, e.g. gelation by calcium ions of alginic acid; crosslinking using a hydrophobic bond, e.g. gelation by heating methyl cellulose or hydroxypropyl cellulose; crosslinking using intermolecular association, e.g. cooling of agar or carageenan to cause the gelation, or the like. The density of crosslinking can impact water absorbability and strength of the resulting gel as well as rate of degradation in vivo. Such crosslinks can be important in associating several phasic constituents of a gel.

However, multiphasic hydrogels can be formed without the use of crosslinking at all and which rely on entanglement. Entanglement and the formation of pseudobonds between hydrophobic segments require the hydrophobic and hydrophilic segments to be covalently bonded together in long structures. The covalent bonding prevents the separation of the hydrophobic and hydrophilic components. The following are patents descriptive of the above background information.

The term "poloxamer" refers to nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade names Pluronics and Kolliphor.

The term "thixotropy" is the property of certain gels or fluids that are viscous under normal conditions, but flow (become less viscous) under shear stress. Some thixotropic gels exhibit a nonNewtonian pseudoplastic flow and a timedependent change in viscosity. A thixotropic fluid is a fluid which takes a finite time to attain equilibrium viscosity when introduced to a step change in shear rate.

The terms "multiphase" and "multiphasic" refer to a gel composition comprise of at least one gel phase and at least one solid phase, and optionally a liquid phase and/or a gas phase. The various phases may be interpenetrating such that mechanically one or more of the phases cannot be separated without altering the gel composition.

The term "cytophylactic polymer" refers to a polymeric system able to direct cellular activity in such a way as to augment the natural cellular processes. These polymers are denominated stimuliresponsive or environmentally sensitive polymers in the sense that they elicit a biologically appropriate response to a wide variety of cellular environments. Temperature, pH, ionic strength and electric field are among the most important stimuli, causing phase or shape changes which dramatically affects the optical, mechanical or transport properties of the present compositions. A number of molecular mechanisms exist which can cause sharp transitions and water plays a crucial role in most of them. These include: ionization, ion exchange, release or formation of hydrophobically bound water and helixcoil transition.

Additionally, diamine groups such a biocompatible lysine can be used at polymerizing links in isocyanate functionalized polymeric backbones, side chains, and biofunctional end groups. Alternatively, the reactive monomer can include a leaving group that can be displaced with a nucleophilic group on a hydrophilic polymer. For example, epichlorohydrin can be used during the polymerization step. The monomer is incorporated into the polymer backbone, and the chloride group is present on the backbone for subsequent reaction with nucleophiles. An example of a suitable hydrophilic polymer containing a nucleophilic group is a polyethylene glycol with a terminal amine group. PEGNH$_2$ can react with the chloride groups on the polymer backbone to provide a desired density of PEGylation on the polymer backbone. Pegylation, in general, is suitable to the botanical extracts of the present invention, since many of them are poorly incorporated in biological tissue, and can be toxic in the absence of hydrophilic modification.

Using the chemistry described herein, along with the general knowledge of those of skill in the art, one can prepare polymer backbones which include suitable leaving groups or nucleophiles for subsequent coupling reactions with suitably functionalized hydrophilicpolymers.

Examples of useful configurations between solid and gel phase gel systems are shown in FIG. 1 although the invention is not limited to such configurations and further configurations using the basic structural units can be provided according to the invention.

FIG. 1 depicts a multiphase gel polymer system 100 of the present invention comprising: a polymeric backbone 102 which defines the overall polymeric morphology of the gel 103 (not drawn to scale), linkage groups 104, side chains 106, and biofunctional end groups 108. The backbone 102 generally comprises hydrophobic 110 and hydrophilic 112 group segments, some or all of which can be biodegradable. Solid phase polymer 113 is depicted as a torus, and comprising pendant hydroxyl groups 115. Linkage groups 104 form bridges 114 between the backbones 102 and solid phase polymer 113, and the solid phase may be of an entirely different composition than the backbone. Typically the bridges comprise linkage groups 104 and side chains 106, wherein the backbones 102 are joined to side chains 106 through linkage groups 104. The biofunctional group 108 may optionally be located on the ends 116 of the backbone 102, on the ends 118 of pendant side chains 120, sandwiched 121 between linkage groups 104 which in turn links to a side chain 106. Biofunctional groups 108 may be located at the junction of two side chains 106 connected by linkage groups 104. It is important to note gel polymer 103 is formed during manufacturing in the presence of solid polymer 113 such that gel 103 passes through, as illustrated at 124, the toroidal opening 126 of solid polymer 113. Thus, the gel fraction 103 is a contiguous macromolecule that interpenetrates the solid polymer 113.

One preferred embodiment is polymers wherein the backbone itself is a polysaccharide, for example hyaluronan. The side chains, for example, may be galactomannan. A particular example involves chains comprising hyaluronan units to which are attached galactomannan side chains functionalized with a diisocyanate linker. Dendritic polymers and comb polymer backbones can be provided by the polymerization product of difunctional and higher functional prepolymers. For example linear chains of polysaccharide pendant hydroxyl groups can be polymerized with triol endcapped with isocyanate groups. These structures can provide a highly crosslinked polymer which would rapidly degrade to low molecular weight components and readily be cleared by the body.

Figure 2:
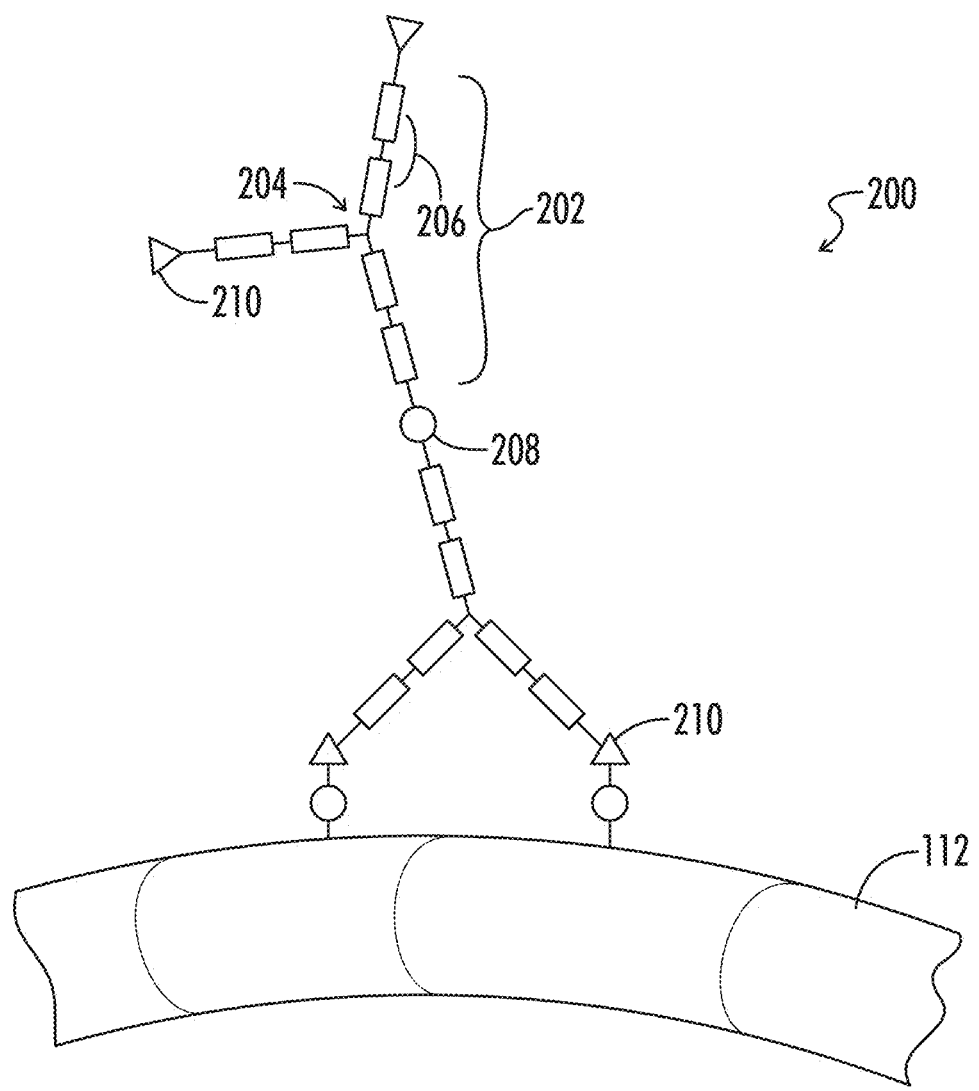
FIG. 2 depicts a bifurcating sequence 200.

For example, FIG. 2 illustrates a bifurcating sequence 200 wherein a polymer backbone 202 has a 3-armed structure 204 comprising two side chains 206. The terminus of each arm of the 3-armed structure 204 is linked to another 3 armed structure 204 through linkage group 208. At the final terminus of the bifurcating structure are located pendant biofunctional groups 210, optionally linked to a solid phase 212. Structures are not drawn to scale.

Figure 3:
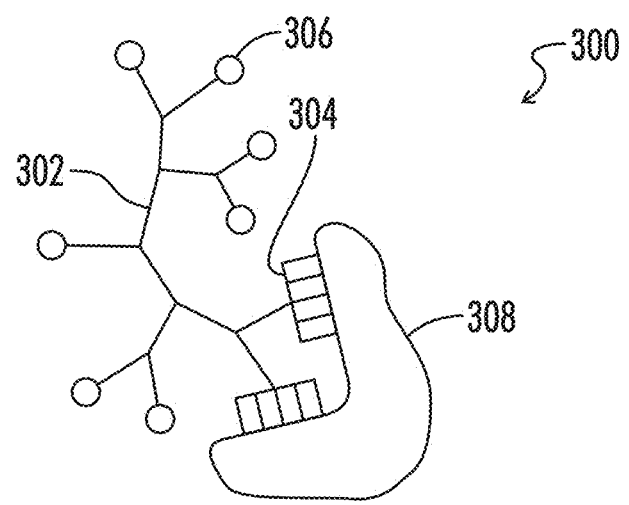
FIG. 3, depicts mixtures 300 of dendritic 302 and comb 304 polymers.

Dendrimers are of particular interest due to their propensity for entanglement and the formation of hydrogels that are relatively stable in the implant environment. Referring to FIG. 3, mixtures 300 of dendritic 302 and comb 304 polymers are possible wherein the dendritic portion serves as a scaffold to the more mobile comb structures. Therefore, the dendritic fraction may be principally endcapped with antiadhesion end groups 306 and the comb fraction may be coupled to a solid phase 308. Alternatively, the comb fraction may be a hyaluronan based gel and the dendritic fraction a poloxamer gel. Polymers containing hyaluronan are known to act as tissue scaffolds, mimicking their biological function in living extracellular matrix.

A further useful backbone structure is comb polymers which contain many side chains extending from a polymer backbone. Polyvinyl alcohol provides a particularly useful backbone for comb polymers. The alcohol groups of polyvinyl alcohol can be esterified and subjected to a carbodiimide linkage chemistry to provide the side chain linkages.
Ligands and Linking Groups Coupled to Biofunctional End Groups Although the principle interest of the present invention is the attachment of biofunctional solid phase to a gel phase, the gel phase may be terminated at least partially with biofunctional molecules. For example, extracts derived from genus *Boswellia* can be bound to the terminal ends of hydrogel structures, other botanical extracts are contemplated. Useful botanicals include, camphenes, camphor, coneole and eucal (derived from *eucalyptus*), moronic acid (derived from pistachio), and like structures.

In particular, polycyclic structures with an odd number of cycles is useful in the present invention. More particularly, chiral polycyclic structures of 3 or 5 rings are of interest. The 5 cyclic structures include, βBoswellic acid, 3O Acetylβboswellic acid, 11Ketoβboswellic acid, 3O Acetyl11ketoβboswellic acid, 11Hydroxyβboswellic acid, 3O Acetoxy11methoxyβboswellic acid, 3O Acetyl11hydroxyβboswellic acid, 9,11Dehydroβboswellic acid, 3O Acetyl9,11dehydroβboswellic acid, αBoswellic acid, 3O Acetylαboswellic acid, Oleanolic acid, Ursolic acid, Baurenol, Lupeol, 11Hydroxyαboswellic acid, 9,11Dehydroαboswellic acid, 3O Acetyl9,11dehydroαboswellic acid, 3Hydroxy8,9,24,25tetradehydrotirucallic acid, 3O Acetyl8,9,24,25tetradehydrotirucallic acid, and 3Oxo8,9,24,25tetradehydrotirucallic acid.
Ratio Considerations in the Gel Phase The density of the hydrophilic side chains along the polymer backbone depends in part on the molecular weight of the side chains. The total percent of the hydrophilic units to the hydrophobic units in the present polymers is between 10 and 50 percent by weight, preferably around 30 percent by weight.

One relevant consideration when determining an appropriate ratio of hydrophilic to hydrophobic units is that the overall polymer, when the hydrophilic side chains are not endcapped with cellsignaling moieties, has some noncell binding properties and preferably incorporates a hallo of water around the polymeric construct when implanted in a mammalian body. A relatively high density of 500 Dalton or less hydrophilic side chains can provide the same degree of resistance to cellular adhesion as a lower density of higher molecular weight side chains. Those of skill in the art can adjust the molecular weight and density of the polymers taking these factors into consideration.
Density of Tethered Biofunctional Solid Phase The side chains of the present invention can be optionally bonded to the solid phases, or polymerized around the solid phases. The solid phase can be cellsignaling regarding its geometrical shape. Chemical ligands can be added to the solid phase in order to elicit specific cell responses. Ligands such as adhesion peptides or growth factors can be covalently or ionically attached to the solid phase or mixed within. A defined fraction of ligandbearing solid phases can be obtained by using appropriate stoichiometric control during the coupling of the ligands to the solid phase, by protecting one or more constituents of the solid phase from reaction with ligands, or by a combination of these approaches. Polymeric Mixtures (both solid and gel phase)

Comb and dendritic polymers can comprise the solid phase as well as the gel phase. When hyaluronan is coupled to a comb or dendritic polymer morphology, cells attach and spread readily on the polymer surface. Accordingly, the solid phase may be coated with these structures. Preferably, cellular proliferation due to the solid is delayed, typically by about 14 days postimplant, so as not to promote tissue adhesion. Adhesion in biological systems is primarily an acute response to a significant disruption of biological structure. Such disruption is associated with release of cytokines that trigger a multiplicity of cellular responses. Given that the gel system is designed to repair or correct the condition responsible for initiation of the acute cellular response, there is a need to down regulate that response, particularly because it tends to be counter to organized cellular repair and healing. Thus, there is a need for a first palliative interval associated with the gel fraction wherein affected tissue surfaces are physically separated, and where the usual cellular communications are disrupted. The requirement is nonspecific, and usually a crude physical barrier is sufficient. However, this deprives the underlying damaged tissue from important nutrient and oxygenation associated with tissue formation. Thus the purpose of the present invention is to initially block using relatively convention gel approaches coupled with a solid aspect that is released in delayed fashion by degradation of the gel fraction or encounter only subsequently by infiltrating tissue, such that a healing response is promoted.

An important aspect in healing is angiogenesis which provides the metabolic capacity for repair. With respect to this second interval of tissue interaction, the degree of cell spreading and proliferation on the surface of the polymeric implant or the release of constituents that induce such a response within the surrounding tissue can be controlled by mixing within the solid phase, relatively hydrophobic copolymers with strongly hydrophilic dendritic or comb polymers.

The size of the biofunctional solid phase and the spatial density of the biofunctional solid phase within the gel is dictated by the rate of absorption of the gel phase.

The copolymers described herein can be blended with other polymers that do not elicit controlled cell responses. In applications where it is desirable to use a biofunctionalized copolymer to modify the surface of a second polymer, the polymers may be processed to achieve segregation of bioactive moieties.

Avoiding a Crystalline State

Returning to the original thesis, wherein a gel system provides order to the healing process and avoids chaotropic effect, it is important to consider the degradation and resorption process of the gel/biological system as a whole. It is recognized that certain clinically useful functionalities, such as the blocking of adhesion formation either by chemotactic sequestration or by physical barrier, are desired; it is important to consider the system as a whole. Many absorbable implants degrade by forming numerous particulate, other absorbables degrade by a surface reaction wherein the tissue exposed surface decreases in molecular weight and forms a diffuse cloud of degradation byproducts. Ideally neither outcome is achieved. A biodegradable implant is preferably dismantled either at the surface or volumetrically in discrete small molecular weight units. In particular, the macroscopic appearance of the implant does not change, but rather its volume decreases. One can imagine the analogy to a hard candy sweet, wherein the candy transitions from a hard solid without a peripheral boundary of diffuse structure. This desired effect can be achieved volumetrically as well, wherein the shape of the implant does not change appreciably, but the tensile strength and molecular weight of the implant diminishes. However, even if this desired result is achieved initially, it is not desirable for the implant to ultimately fractionate. It is more desirable for the tensile strength to decrease and the final product to be in a gellike state and highly tenuous without fractionation.

Accordingly, the solid phase should not contribute to the ultimate fractionation of the gel system in vivo. More particularly, the solid phase should not act as a nidus for fractionation of the implant. If the implant should ultimately fractionate, the resulting particulate formation should have a modulus substantially below that of tissue. There are two ways to achieve this endpoint. Firstly, the solid phase transforms into the gel phase, and the resulting gel phase resorbs in a homogeneous fashion analogous to the original gel phase. Secondly, the solid phase becomes a structural element of the healing tissue. For example, solid fibrils within the gel are comprising a cellular constituent, for example hyaluronan, wherein they are directly incorporated into the tissue structure. In other aspects, the solid phase is fed upon by cells, providing both a directional stimulus and a nutrient or chemical advantage to local cells. Thus, the solid phase can be considered a nutrient or chemical supplement that aids in regenerative processes. Such supplemental effects may include cellular signaling, both at the energetic level and at the amino acid instructional level.

In consideration of the above, if the solid phase is small enough, fractionation of the implant by release of a solid phase is not necessarily disadvantageous, especially when such release in original form or a degraded form, stimulates a path that results in reduced disorder of the regenerating tissue.

In particular, the desired function of an implant is not to create boundaries between tissues, since essentially the human body is a freely intercommunication structure. Processes leading to formation of fibrotic encapsulation, especially encapsulants that are devoid of blood vessels, create zones that are segregated from the normal immunological protections of the body. Such zones have been shown clinically to be sites of endogenous infection, sometimes many years after implantation.

Large scale crystalline structures within the body are nonbiologic, generally. Any process that results in the formation of atomically dense polyhedral molecular structures is to be avoided. These structures can be individual, or comprise a macroscopic volume. However, their density and strong internal binding, resulting in the regular geometric shape, are inhibitory to cellular processes. They are identified as foreign, and incite a strong foreign body response which creates a multiplicity of avascular tissue encapsulations. These encapsulations are benign at the time of their formation, but are problematic in the long term since they are not connected to the protective and restorative processes of living tissue.

In the case of amorphous degradation, generally this mode of resorption is preferred since the low density at the periphery allows for some degree of cellular infiltration. In the late stage of degradation, this cellular infiltration is associated with a low degree of inflammation, primarily due to the absence of a welldefined implant border. While it is preferred that the solid phase contribute positively to the ordered regeneration of the affected tissue, in absence of this ideal, a reduced foreign body reaction and a low level of inflammatory activity is much preferred to usual modes of implant resorption.

Long-Term Lubricants in the Body

There are many clinical applications where a long term lubricant, especially at joint surfaces would be beneficial. Unfortunately, no implantable gel, whether comprises absorbable or nonabsorbable chemical units, is permanent. The body is essentially self-maintaining. There is not biologic locus where a lubricating substance persists for the life of the individual. It is unrealistic to expect a longterm synthetic material to exceed the capabilities of the regenerative biologic system. The best outcome is the restoration of functionality to the site, and in many cases this entails reduction of an inflammatory response that in most cases results in separation of tissue volumes and the inhibition of restorative processes.

However, the repair process can be of long duration, especially in those situations where blood supply is low. For example, tendons are a classic example of high stress low metabolic activity. In this situation, the tendon can actually be compromised further by the addition of fibrotic tissue, resulting in an increasingly more painful situation.

Accordingly, it may be useful, but not necessarily physiologic, to provide a lubricant that may act beyond organic moieties to reduce stressrelated degradation of an already compromised biologic tissue. In these situations the pressures/stresses may be extreme for short durations. There is need for a shock absorber functionality. For example, consider a gel phase that serves the purpose of providing lubricity and a degree of separation between injured tissue, which without separation may be joined by tissue and compromised further. In this case, even if the addition of solid particulate to the gel construct does not aid in maximum freedom of movement, its function as a solid, and not easily deformed from its designed shape, makes it ideal as a shock absorber. Thus in those situation where stress is extreme and local, and normal gels would be thinned to the point of being ineffective, a residual solid particulate fraction would provide a high modulus layer of protection, wherein surfaces do not abrade or impart their maximum kinetic energy. In this situation, the particulate fraction serves only an auxiliary function, they do not contribute to wound repair but rather provide a safeguard, wherein when forces exceed a certain threshold they prevent a bottoming action that may result in further tissue degradation. In the case where the gel is quickly resorbed in one fraction, a second gel fraction can be of longer duration of small volume, and principally serving as a coupling mechanism between particles, where in the final stages there is remaining only a thin layer of less resorbable gel coupling a solid phase with a clinically useful modulus not achieved in the bulk gel implantation.

Adherent Gel Systems

The primary dislocation of gels implanted in the body for a specific function is the effect of gravitational slumping. Stated simply, the lower energy state of any sufficiently dense implant, is for the implant to migrate to lower elevations within the body. This slumping effect can be exacerbated by the presence of defects or voids between tissue layers. In many cases, the slumping of an implanted gel results in the gel being displaced to a location where pressures are low and where the gel is essentially not needed. Furthermore, in cases where the gel pools into generally spherical volumes, the implant can result in regions where microbial growth is sequestrated from normal cellular protective mechanism. Thus, there is a need for a gel implant to retain its shape, and more importantly adhere to the tissue surfaces designated by a surgeon.

Gravitational slumping can be avoided to a considerable degree by engineering a preferred shape into the gel construct. However, that shape is not always a priori known, and a surgeon would like the implant to assume the shape of the tissue to which it is applied. In this case, an in situ polymerizing gel construct offers several advantages. Given the extremely challenging regulatory environment for in situ polymerizing products, other avenues are commercially more viable.

For example, mucoadhesive systems have been considered. They offer good initial localization of an implant. However, longer term, the fluids present in the body equilibrate with the van der Waals forces essential to the mucoadhesive functionality and eventually render mucoadhesivity ineffective. In many cases a shortterm adhesive functionality is clinically useful, and many polysaccharide compositions of the present invention fulfill this need.

However, there is a need for an implant localizing mechanism which is not rendered ineffective by the body. Such methodologies, in the absence of chemical bonding, constitute high energy surfaces, which precipitate a protein denaturation, and consequently a permanent localization of a surface with respect to tissue.

Generally, as described previously, denaturation of proteins is not a desired outcome. However, when it is surface specific, and of limited volume its utility exceeds is disadvantages. To this end, it is instructive to consider the biological world, and in particular superhydrophobic surfaces. For example, in the case of a rose petal, a droplet is immobilized on the rose petal surface. This effect, known as the CassieWenzel effect relies on a three phase juxtaposition between the solid of the petal surface, the liquid in a spherical geometry, and the air which serves to localized the liquid/solid interface my means of a nanostructure.

In the body we do not have three phases available, gases are absent. However, there is a distinction to be made between polar water and hydrophobic substances such as oils and fats. In the body, there is an abundance of segregated hydrophobic and hydrophilic domains. These substances behave similarly to the relationship between gas and solids. They essentially do not interact. Thus when a structure is juxtaposed between two nonreacting media, such as water between as solid/gas interface, the results can be localization of the water. In the case of living tissue, a substance can be interposed between the hydrophilic and hydrophobic constituents of the body. That substance must possess a hierarchy of structural surfaces, some of which are predisposed to attracting the hydrophilic fraction and other which is predisposed to attracting the hydrophobic fraction. Thus we define a liquidliquid analogue to the CassieWenzel effect, wherein the essential geometry remains the same.

The present invention discloses an novel tissue adherent mechanism, analogous to the CassieWenzel effect in air, whereby the differences in surface energy between the two constituents creates a localization of the implant in vivo which is not saturated in the body.

Additionally, wherein the localization is maintained for an extended period, the surface texture may additionally serve as a tissue scaffolding technology. Accordingly, not all of the solid phase surface need be devoted to a localization effect, other surface elements or other surface particulates may be devoted to the scaffolding aspect.

In summary, there are three ways to localize a gel in situ: 1) sticky, e.g., mucoadhesive, 2) frictional, the opposite of lubricious, and 3) in situ polymerizing, where bonds are formed between implant and living tissue.

Entropic Considerations

Any system liberating heat increases the entropy of that system. In the body, the healing process liberates large amount of heat, both in the reparative process and in the degradation of failed cellular constituents. It is a challenge in the medical sciences to enhance the healing process without increasing it entropy.

Historically, the case of mesh augmented soft tissue repair is instructive. Initially it was thought that placing an antagonistic material in the body, such as polypropylene, would enhance the healing process by increasing the energy dissipation at the wound site by an upregulated foreign body response. While increase heat output and increased cellular activity were achieved, these endpoints did not result in product wound healing.

In the case where dense encapsulation occurred due to the antagonistic nature of the implant material, blood supply was eliminated or severely curtailed to the implant site. As a result, bacteria which preferentially adhere to such high energy sites, proliferated, whether they be there as a result of the initial implantation or by an endogenous source.

It is noteworthy to recognize that in such environments, bacterial counts too low to exceed the normal bodily responses exceed them in such a high energy environment. The combination of high surface energy, necrotic tissue debris, and the inhibit of regular antimicrobial cellular processes, results in a highly disorder wound repair, as well as possible systemic adverse events.

This clinical experience has resulted in the generally accepted belief that less is more, and that mesh prosthetics intended to strengthen soft tissue defects are beneficially constructed when they contain less material, leading to the now generally accepted criterion of areal density. Reduced areal density is considered a positive, although this results in a vastly decreased tensile strength. Thus the original intension of soft tissue augmentation prosthetics has be supplanted by the desire for a more normal and ordered repair. The reason for this is that disordered repairs often fail since they are not metabolically viable. Common to both concerns is the avoidance of dense, avascular tissue that shields the implant from antimicrobial processes and also prevents an ordered repair of the tissue site.

While the gels of the present invention are not intended to provide a reinforcing benefit initially, they can achieve this result in the longer term. There is presently no successful replacement for tissue to correct a tissue defect. Synthetics undergo encapsulation, shrinkage, and ultimately provide no support to the affect region. Biologics degrade quickly, and provide only minimal support during their short tenure within the body. In fact, these approaches have been fundamentally misdirected in that they seek to provide a mechanical enhancement, while neglecting the fact that such mechanical enhancement is fundamentally opposed to normal tissue restoration. These repairs have certainly found utility in extremely pathologic cases or in individuals where normal healing is compromised. But far too often, these mesh are implanted in individuals where a simple suture repair of the defect would suffice; and this is especially true in women of childbearing age where regenerative processes are naturally elevated.

One can appreciate the truth in the concept of "less is more", if that concept means no mechanical support is more. In essence, what is needed in healthy individuals is a support for normal healing, and not a replacement. Necessarily, to support a site means to be present at a site, and one of the main disadvantages of current gel technologies is that they gravitationally migrate from the site needing support. The support is not one of reducing forces or bridging tissue layers. The support is one of correcting the abiological instance of surgical intervention. While the actual treatment of the defective tissue site may be beneficial, surgically getting to that site initiates a cascade of cellular responses that are, at least in the short term, deleterious. For example, infection is never a concern for individuals that rejuvenate without the need for surgical intervention. Similarly remodeling of tissue, and the ballingup of surgical implants never occurs in injured tissue without the presence of a prosthetic. These observations indicate that promoting healing is more beneficial to a patient that mechanically reinforcing a soft-tissue defect.

In short, there is no methodology at present that supersedes the effectiveness of normal tissue repair. In considering this observation, what differentiates normal tissue repair from synthetic tissue augmentation? If one looks at the tissue site 3 months after the initial insult in any repair where normal healing occurs and synthetic augmentation was instituted, it is always the case that in the normal healing instance the entropic state or the ordered appearance of the tissue is always greater in the normal healing case. This is not to say that there are not cases where the tissue defect is so extreme that it can be repaired by normal processes. Thus, whether one advocates for minimal surgical intervention or otherwise, the main criteria for success are not how strong the repair methodology is, but rather the orderliness of the repair, and this is supported by the recent popularity in using reduced areal density mesh, even though these mesh are insufficient in cases where the normal reparative mechanism is insufficient.

It is not sufficient to not interfere in the normal healing process, if that was sufficient surgeons would never have opted for the various tissue augmentation methodologies available on the market. Thus, beyond the need to block adverse tissue layer to tissue layer adhesion, there is a greater need to promote and accelerate normal tissue healing mechanism. Chief among these criteria are the need for blood supply, because without blood supply no metabolic mechanism can be employed in tissue repair. In fact, it is likely in all situations that a prosthetic that promotes blood delivery to a region accomplishes more than any other therapeutic treatment regarding optimal repair of soft tissue defects Clinically the industry has concentrated on pain, and not surprisingly, since all synthetic interventions provide a short term mechanical benefit at the cost of long term insufficiency on many levels. Long term risk/benefit is just now being realized. To avoid the long term adverse events one must minimize the synthetic intervention, even if it means compromising tissue repair in the short term and this is essentially the program currently in vogue concerning light weight mesh. However, merely reducing the chaotropic effect is not in itself a benefit.

To be clinically useful, the implant must provide an ordering effect, not in terms of setting things identically, but in terms of providing continuity to the surrounding tissue structure. Thus, establishing order in a biologic system does not mean simplifying, or minimizing variability, it simply means matching the dimensional aspects of the surrounding tissue. The dimensional aspects being the number and range of hierarchical structures present in tissue, understanding the energetic and fluid mechanical needs of living cells, and stemming the short term needs without disrupting the normal cellular repair process. There are clearly enhancements over these essential needs, many of which are currently under study, and therefore we include in this largely physical set of considerations the biological considerations regarding the chemical signaling of cells.

Drug Delivery Aspect

In another aspect of the invention, the multiphasic gel comprises a biofunctional molecule at a concentration from about 5% to about 50% of the implant by weight. The molecule may be incorporated in the gel fraction if it is water soluble, and in the solid fraction if not water soluble. The gel phase may be loaded with excipients to control drug release both from the solid phase and the gel phase. Excipients useful in the present invention are tocopherol isomers and/or their esters; tocotrienols and/or their esters; benzyl alcohol; benzyl benzoate; those dibenzoate esters of poly(oxyethylene) diols having low water solubility; dimethyl sulfone; poly(oxypropylene) diols having low water solubility; the mono, di, and triesters of Oacetylcitric acid with straight and branched chain aliphatic alcohols; and liquid and semisolid polycarbonate oligomers.

The biofunctional agent of the present invention is selected from the group consisting of analgesics, anesthetics, narcotics, angiostatic steroids, anti-inflammatory steroids, angiogenesis inhibitors, nonsteroidal antiinflammatories, antiinfective agents, antifungals, antimalarials, antitublerculosis agents, antivirals, alpha androgenergic agonists, beta adrenergic blocking agents, carbonic anhydrase inhibitors, mast cell stabilizers, miotics, prostaglandins, antihistamines, antimicrotubule agents, antineoplastic agents, antipoptotics, aldose reductase inhibitors, antihypertensives, antioxidants, growth hormone agonists and antagonists, vitrectomy agents, adenosine receptor antagonists, adenosine deaminase inhibitor, glycosylation antagonists, anti aging peptides, topoisemerase inhibitors, antimetabolites, alkylating agents, antiandrigens, antioestogens, oncogene activation inhibitors, telomerase inhibitors, antibodies or portions thereof, antisense oligonucleotides, fusion proteins, luteinizing hormone releasing hormones agonists, gonadotropin releasing hormone agonists, tyrosine kinase inhibitors, epidermal growth factor inhibitors, ribonucleotide reductase inhibitors, cytotoxins, IL2 therapeutics, neurotensin antagonists, peripheral sigma ligands, endothelin ETA/receptor antagonists, antihyperglycemics, antiglaucoma agents, antichromatin modifying enzymes, insulins, glucagonlikepeptides, obesity management agents, anemia therapeutics, emesis therapeutics, neutropaenia therapeutics, tumorinduced hypercalcaemia therapeutics, blood anticoagulants, immunosuppressive agents, tissue repair agents, psychotherapeutic agents, botulinum toxins (Botox, Allergan), and nucleic acids such as siRNA and RNAi.

Specific areas of the human or animal body to be targeted for injection or implantation or topical applications of these multiphasic gel system include, but are not limited to: heart, brain, spinal nerves, vertebral column, skull, neck, head, eye, ear organs of hearing and balance, nose, throat, skin, viscara, hair, shoulder, elbow, hand, wrist, hip, knee, ankle, foot, teeth, gums, liver, kidney, pancreas, prostate, testicles, ovaries, thymus, adrenal glands, pharynx, larynx, bones, bone marrow, stomach, bowel, upper and lower intestines, bladder, lungs, mammaries.

The multiphasic gel system according to the present invention has particular applicability in providing a controlled and sustained release of active agents effective in obtaining a desired local or systemic physiological or pharmacological effect relating at least to the following areas: treatment of cancerous primary tumors, chronic pain, arthritis, rheumatic conditions, hormonal deficiencies such as diabetes and dwarfism, modification of the immune response such as in the prevention and treatment of transplant rejection and in cancer therapy.

The system is also suitable for use in treating HIV and HIV related opportunistic infections such as CMV, toxoplasmosis, pneumocystis carinii and mycobacterium avium intercellular. The system may be used to create layers between tissue, in particular between layers of tissue modified by surgical intervention in order to direct or stimulate healing and the separate adjacent tissue layers that would be compromised by the formation of adhesions.

Other uses of the formulations include, for example, mediating homograft rejection with formulations comprising surolimus or cyclosporine. Local cancer therapy may be delivered to, for example, the kidney or liver, using in formulations comprising, for example, adriamycin or small epidermal growth factors. Prostate cancer may be treated with formulations including fenasteride. Cardiac stents implants, central nervous system implants (e.g., spinal implants), orthopedic implants, etc., may be coated with formulations including growth or differentiation factors, anti-inflammatory agents, or antibiotics. In particular, botanical extracts known to possess antimicrobial or healing stimulative properties are useful.

Suitable classes of active agents for use in the system of the present invention include, but are not limited to the following: peptides and proteins such as cyclosporin, insulins, glucagon-like peptides, growth hormones, insulin related growth factor, botulinum toxins, and heat shock proteins; anesthetics and pain killing agents such as lidocaine and related compounds, and benzodiazepam and related compounds; anticancer agents such as 5-fluorouracil, methotrexate and related compounds; anti-inflammatory agents such as 6-mannose phosphate; Antifungal agents such as fluconazole and related compounds; antiviral agents such as trisodium phosphomonoformate, trifluorothymidine, acyclovir, cidofovir, ganciclovir, DDI and AZT; cell transport/ mobility impending agents such as colchicines, vincristine, cytochalasin B and related compounds; anti-glaucoma drugs such as beta-blockers: timolol, betaxolol atenolol; immunological response modifiers such as muramyl dipeptide and related compounds; steroidal compounds such as dexamethasone, prednisolone, and related compounds; and carbonic anhydrase inhibitors.

It is also contemplated that these multiphasic gel formulations can be coatings on implanted surfaces, such as but not limited to, those on catheters, stents (cardiac, CNS, urinary, etc.), prothesis (artificial joints, cosmetic reconstructions, and the like), tissue growth scaffolding fabrics, or bones and teeth to provide a wide variety of therapeutic properties (such as but not limited to, anti-infection, anti-coagulation, anti-inflammation, improved adhesion, improved tissue growth, improved biocompatibility).

These surfaces can be from a wide variety of materials, such as but not limited to, metals, polyethylene, polypropylene, polyurethanes, polycarbonates, polyesters, poly(vinyl acetates), poly(vinyl alcohols), poly(oxyethylenes), poly(oxypropylenes), cellulosics, polypeptides, polyacrylates, polymethacrylates, polycarbonates and the like.

Active agents, or active ingredients, that may be useful in the present invention, as determined by one of ordinary skill in the art in light of this specification without undue experimentation, include but are not limited to:

Analgesics, Anesthetics, Narcotics such as acetaminophen; clonidine (Duraclon Roxane) and its hydrochloride, sulfate and phosphate salts; oxycodene (Percolone, Endo) and its hydrochloride, sulfate, phosphate salts; benzodiazepine; benzodiazepine antagonist, flumazenil (Romazicon, Roche); lidocaine; tramadol; carbamazepine (Tegretol, Novartis); meperidine (Demerol, SanofiSynthelabo) and its hydrochloride, sulfate, phosphate salts; zaleplon (Sonata, WyethAyerst); trimipramine maleate (Surmontil, WyethAyerst); buprenorphine (Buprenex, Reckitt Benckiser); nalbuphine (Nubain, Endo) and its hydrochloride, sulfate, phosphate salts; pentazocain and hydrochloride, sulfate, phosphate salts thereof; fentanyl and its citrate, hydrochloride, sulfate, phosphate salts; propoxyphene and its hydrochloride and napsylate salts (Darvocet, Eli Lilly& Co.); hydromorphone (Dilaudid, Abbott) and its hydrochloride, sulfate, and phosphate salts; methadone (Dolophine, Roxane) and its hydrochloride, sulfate, phosphate salts; morphine and its hydrochloride, sulfate, phosphate salts; levorphanol (Levodromoran, ICN) and its tartrate, hydrochloride, sulfate, and phosphate salts; hydrocodone and its bitartrate, hydrochloride, sulfate, phosphate salts;

Angiostatic and/or Antiinflammatory Steroids such as anecortive acetate (Retaane®, Alcon, Inc., Fort Worth, Tex.); tetrahydrocortiso; 4,9(11)-pregnadien-17-α-21-diol-3,20-dione (Anecortave) and its 21-acetate salt; 11-epicortisol; 17-α-hydroxyprogesterone; tetrahydrocortexolone; cortisone; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its 21-acetate, 21-disodium phosphate, and 21-hemisuccinate forms; triamcinolone benetonide; triamcinolone hexacetonide; fluocinolone and fluocinolone acetate; dexamethasone and its 21-acetate, 21-(3,3dimethylbutyrate), 21-phosphate disodium salt, 21-diethylaminoacetate, 21-isonicotinate, 21-dipropionate, and 21-palmitate forms; betamethasone and its 21-acetate, 21-adamantoate, 17-benzoate, 17,21-dipropionate, 17-valerate, and 21-phosphate disodium salts; beclomethasone; beclomethasone dipropionate; diflorasone; diflorasone diacetate; mometasone furoate; and acetazolamide (Diamox® Lederle Parenterals, Inc., Carolina, Puerto Rico; several other manufacturers); 21-nor-5-β-pregnan 3-α-17-α-20-triol-3-acetate; 21-nor-β-pregnan-3-α-17-α-20-triol-3-phosphate; 21-nor-5-β-pregn-17-20)en-3-α-,16-diol; 21-nor-5-β-pregnan-3-α-, 17-β-,20-triol; 20-acetamide-21-nor-5-β-pregnan 3-α-,17-α-diol-3-acetate; 3-β-acetamido-5-β-pregnan-11-β-,17-α-, 21-triol-20-one-21-acetate, 21-nor-5-α-pregnan-3-α-17-β-20-triol; 21-α-methyl-β-pregnan-3-α-,11-β-17-α-21-tetrol-20-one-21-methyl ether; 20-azido-21-nor-5-β-pregnan-3-α-,17-α-diol; 20-(carbethoxymethyl)-thio-21-nor-5-β-pregnan-3-α-.,17-α-diol; 20-(4-fluorophenyl)-thio-21-nor-5-β-pregnan-3-α-17.alpha.diol; 16-α-(2-hydroxyethyl)-17-β-methyl-5-β-androstan-3-α-,17-α-diol; 20-cyano-21-nor-5-ω-pregnan-3-α-,17-α-diol; 17-α-methyl-5-β-androstan-3-α-.,17-β-diol; 21-nor-5-β-pregn-17-(-20)en-3-α-ol; 21or5-β-pregn-17(20)en-3-α-ol-3-acetate; 21-nor-5-pregn-17(20)-en-3-α-ol-16-acetic acid 3-acetate; 3-β-azido-5-β-pregnan-11-β-,17-α-,21-triol-20-one-21-acetate; an 5-β-pregnan-11-β-17-α-,21-triol-20-one; 4-androsten-3one-17-β-carboxylic acid; 17-α-ethynyl5(10)estren17-β-ol3one; and 17-α-ethynyl1,3,5(10)estratrien3,17-β-diol.

Nonsteroidal Antiinflammatories such as naproxin; diclofenac; celecoxib; sulindac; diflunisal; piroxicam; indomethacin; etodolac; meloxicam; ibuprofen; ketoprofen; flurbiprofen (Myriad); mefenamic; nabumetone; tolmetin, and sodium salts of each of the foregoing; ketorolac bromethamine; ketorolac bromethamine tromethamine (Acular®, Allergan, Inc.); choline magnesium trisalicylate; rofecoxib; valdecoxib; lumiracoxib; etoricoxib; aspirin; salicylic acid and its sodium salt; salicylate esters of alpha, beta, gammatocopherols and tocotrienols (and all their d, l, and racemic isomers); methyl, ethyl, propyl, isopropyl, nbutyl, secbutyl, tbutyl, esters of acetylsalicylic acid.

Angiogenesis Inhibitors such as squalamine, squalamine lactate (MSI1256F, Genaear) and curcumin; Vascular Endothelial Growth Factor (VEGF) Inhibitors including pegaptanib (Macugen, Eyetech/Pfizer); bevacizumab (Avastin, Genentech/generic); Neovastat (Aeterna); PTK 787 (Schering/Novartis); Angiozyme (RibozymeChiron); AZD 6474 (AstraZeneca); IMC1C11 (Imclone); NM3 (ILEX Oncology); 56668 (Sugen/Pharmacia); CEP7055 (Cephalon); and CEP5214 (Cephalon); Integrin Antagonists such as Vitaxin (Applied Molecular Evolution/Medimmune); S 137 (Pharmacia); 5247 (Pharmacia); ST 1646 (Sigma Tau); DPC A803350 (BristolMyers Squibb); and oguanudines (3D Pharmaceuticals/generic); matrix metalloproteinase inhibitors such as prinomastat (AG 3340, Pfizer/generic), (ISV616, InSite Vision), (TIMP3, NIH); 53304 (Shionogi); BMS 275291 (Celltech/BristolMyers Squibb); SC 77964 (Pharmacia); ranibizumab (Lucentis, Genentech); ABT 518 (Abbott); CV 247 (Ivy Medical); shark cartilage extract (Neovastat, Aeterna); NX278L antiVEGF aptamer (EyeTech); 2'Omethoxyethyl antisense Craf oncogene inhibitor (ISIS13650) vitronectin and osteopontin antagonists (3D Pharm); combretstatin A4 phosphate (CA4P, Oxigene); fab fragment .alpha.V/beta.1 integrin antagonist (Eos200Protein Design Labs); .alpha.v/. beta.3 integrin antagonist (Abbott); urokinase plasminogen activator fragment (A6, Angstrom Pharm.); VEGF antagonist (AAVPEDF, Chiron); kdr tyrosine kinase inhibitor (EG3306, Ark Therapeutics); cytochalasin E (NIH); kallikrininbinding protein (Med. Univ. So. Carolina); combretastatin analog (MV540, Tulane); pigmentepithelium derived growth factor (Med. Univ. SC); pigmentepithelium derived growth factor (AdPEDF, GenVec/Diacrin); plasminogen kringle (Med. Univ. SC); rapamycin; cytokine synthesis inhibitor/p38 mitogenactivated protein kinase inhibitor (SB220025, GlaxoSmithKline); vascular endothelial growth factor antagonist (SP (V5.2)C, Supratek); vascular endothelial growth factor antagonist (SU10944, Sugen/Pfizer); vascular endothelial growth factor antagonist.

Antiinfective Agents such as Antibacterials including aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; rifampin; dapsone atovaquone; rifabutin; linezolide; polymyxin B and its hydrochloride, sulfate, or phosphate salt; sulfacetamide and its sodium salt; minocycline; and clarithromycin:

Antifungals such as amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Antimalarials such as chloroquine and its hydrochloride, sulfate or phosphate salt; hydroxychloroquine and its hydrochloride, sulfate or phosphate salt; mefloquine and its hydrochloride, sulfate, or phosphate salt; atovaquone; proguanil and its hydrochloride, sulfate, or phosphate salt forms.

Antituberculosis Agents such as ethambutol and its hydrochloride, sulfate, or phosphate salt forms; aminosalicylic acid; isoniazid; pyrazinamide'; ethionamide.

Antivirals such as amprenavir; interferon alfan3; interferon alfa2b; interferon alfacon1; peginterferon alfa2b; interferon alfa2a; lamivudine; zidovudine; amadine (Symmetrel, Endo) and its hydrochloride, sulfate, and phosphate salts; indinavir and its hydrochloride, sulfate, or phosphate salt; ganciclovir; ganciclovir sodium salt; famciclovir; rimantadine and its hydrochloride, sulfate, or phosphate salt; saquinavir; valacyclovir and its hydrochloride, sulfate, or phosphate salt; zinc ester complexes; and zin; acetoacetonate or zinc acetoacetic ester complexes.

Anti HIV/AIDS agents including stavudine, reverset (Pharmasset), ACH126443 (Achillion), MIV310 (Boehringer Ingelheim), ZeritlR(d4tT) (BristolMeyers Squibb) Ziagen (GlaxoSmithKline), Viroad (Glead), hivid (Roche), Emtriva (Gilead), delavirdine (Pfizer), AG1549 (Pfizer), DPC083 (BristolMyers Squibb), NSC675451 (Advanced Life Sciences), IMC125 (Tibitec), azidicarbonamide, GPGNH2 (Tripep), immunitin (Colthurst), cytolin (Cytodyn), HRG21 (Virionyx), MDX010 (Gilead), TXUPAP (Wayne Hughes Inst), proleukin (Chiron), BAY 504798 (Bayer), BG777 (Virocell), Crixivan (Merck), Fuzeon (HoffLaRoche), WF10 (Oxo Chemie), Ad5 Gag vaccine (Merck), APIA00003 and 047 (Wyeth), Remunex (Immune Response Corp.), MVABN Nef (Bavarian Nordic), GTU MultyHIV vaccine (FIT Biotech).

Insulins such as Novolog (aspart), Novolin R, Novolin N, Novolin L, Novolin 70/30, and Novolog 70/30 (Novo Nordisk); Humalog (lispro) Humulin R, Humulin N, Humulin L, Humulin 50/50 and 70/30, and Humalog Mix 75/25 and 70/30 (Eli Lilly); Ultralente (Eli Lilly); Lantus (glargine, Aventis); porcine; and bovine insulins.

Glucagonlike Peptide1 (Glp1) and analogs (for diabetes therapy and appetite suppression, cardiac protection) (see Keiffer et al., 20 Endocr Rev., 876913 (1999) Glp1 Receptor stimulators such as exendin4, Exenatide and Exenatide LAR (Amylin Pharma); Liraglutide (Novo Nordisk); ZP10 (Zealand Pharma); Glp1albumin (Conjuchem); and DpplV inhibitors (which inhibit enzyme attack on Glp1) such as LAF237 (Novartis); MK0431 (Merck); BMS477188 (BristolMyers Squibb); and GSK23A (GlaxoSmithKline);

Alpha Androgenergic Agonist such as brimonidine tartrate; Beta Adrenergic Blocking Agents such as betaxolol and its hydrochloride, sulfate, or phosphate salt; levobetaxolol and its hydrochloride, sulfate, or phosphate salt; and timolol maleate.

Carbonic Anhydrase Inhibitors such as brinzolamide; dorzolamide and its drochloride, sulfate, or phosphate salt; and dichlorphenamide.

Mast Cell Stabilizers such as pemirolast and its potassium salt; nedocromil and its sodium salt; cromolyn and its sodium salt.

Miotics (Cholinesterase Inhibitors) such as demecarium bromide.

Prostaglandins such as bimatoprost; travoprost; and latanoprost.

Antihistamines such as olopatadine and its hydrochloride, sulfate, or phosphate salt forms; fexofenadine and its hydrochloride, sulfate, or phosphate salt; azelastine and its hydrochloride, sulfate, or phosphate forms; diphenhydramine and its hydrochloride, sulfate, or phosphate forms; and promethazine and its hydrochloride, sulfate, or phosphate forms.

Antimicrotubule Agents such as Taxoids including paclitaxel (Taxol, BristolMyers Squibb); vincristine (Oncovin, Eli Lilly & Co.) and its hydrochloride, sulfate, or phosphate salt forms; vinblastine (Velbe, Eli Lilly & Co.) and its hydrochloride, sulfate, or phosphate salt; vinorelbine (Novelbinr, Fabre/GSK); colchicines; docetaxel (Taxotere, Aventis); 109881 (Aventis); LIT 976 (Aventis); BMS 188797 (BristolMyers Squibb); BMS 184476 (BristolMyers Squibb); DJ 927 (Daiichi); DHA paclitaxel (Taxoprexin, Protarga); Epothilones including epothiloneB (EPO 906, Novartis/generic); BMS 247550 (BristolMyers Squibb); BMS 310705 (BristolMyers Squibb); epothilone D (KOS 862, Kosan/generic); and ZK EPO (Schering AG).

Antineoplastic agents such as doxorubicin and its hydrochloride, sulfate, or phosphate salt; idarubicin and its hydrochloride, sulfate, or phosphate salt; daunorubicin and its hydrochloride, sulfate, or phosphate salt; dactinomycin; epirubicin and its hydrochloride, sulfate, or phosphate salt; dacarbazine; plicamycin; mitoxantrone (Novantrone, OSI Pharmaceuticals) and its hydrochloride, sulfate, or phosphate salt; valrubicin; cytarabine; nilutamide; bicalutamide; flutamide; anastrozole; exemestane; toremifene; femara; tamoxifen and tamoxifen citrate; temozolimide (Temador); gemcitabine and its hydrochloride, sulfate, or phosphate salt; topotecan and its hydrochloride, sulfate, or phosphate salt; vincristine and its hydrochloride, sulfate, or phosphate salt; liposomal vincristine (OncoTCS, Inex/Elan); methotrexate and methotrexate sodium salt; cyclophosphamide; estramustine sodium phosphate; leuprolide and leuprolide acetate; goserelin and goserelin acetate; estradiol; ethinyl estradiol; Menest esterified estrogens; Premarin conjugated estrogens; 5flurouracil; bortezamib (Velcade, Millenium Pharmaceuticals).

Antiapoptotics such as desmethyldeprenyl (DES, RetinaPharma).

Aldose Reductase Inhibitors such as GP1447 (Grelan); NZ314 (parabanic acid derivative, Nippon Zoki); SG210 (Mitsubishi Pharma/Senju); and SJA705 (Senju).

Antihypertensives such as candesartan cilexetil (Atacand/Biopress, Takeda/AstraZeneca/Abbott); losartan (Cozaar, Merck); and lisinopril (Zestril/Prinivil, Merck/AstraZeneca).

Antioxidants such as benfotiamine (Albert Einstein Col. Of Med./WorWag Pharma); ascorbic acid and its esters; tocopherol isomers and their esters; and raxofelast (IRFI005, Biomedica Foscama);

Growth Hormone Antagonists such as octreotide (Sandostatin, Novartis); and pegvisomant (Somavert, Pfizer/Genentech); Vitrectomy Agents such as hyaluronidase (Vitrase, ISTA Pharm./Allergan);

Adenosine Receptor Antagonist such as A2B adenosine receptor antagonist (754, Adenosine Therapeutics);

Adenosine Deaminase Inhibitor such s pentostatin (Nipent, Supergen);

Glycosylation Antagonists such as pyridoxamine (Pyridorin, Biostratum);

Anti-Ageing Peptides, such as AlaGluAspGly (Epitalon, St Petersburg Inst. Biyreg. and Geron).

Topoisomerase Inhibitors such as doxorubicin (Adriamycin/Caelyx, Pharmacia/generics); daunorubicin (DaunoXome, Gilead/generics); etoposide (Vepecid/Etopophos, BristolMyers Squibb/generics; idarubicin (Idamycin, Pharmacia); irinotecan (Camptosar, Pharmacia); topotecan (Hycamtin, GlaxoSmithKline); epirubicin (Ellence, Phamacia); and raltitrexed (Tomudex, AstraZeneca).

Antimetabolites such as methotrexate (generic) and its sodium salt; 5fluorouracil (Adrucil, ICN Pharmacia); cytarabine (Cytosar, Pharmacia/generic); fludarabine (Fludara, Schering) and its forms as salts with acids; gemcitabine (Gemsar, Eli Lilly& Co.); capecitabine (Xeloda, Roche); and perillyl alcohol (POH, Endorex).

Alkylating Agents such as chlorambucil (Leukeran, GlaxoSmithKline); cyclophosphamide (Cytoxan, Pharmacia/BristolMeyers Squibb); methchlorethanine (generic); cisplatin (Platinal, Pharmacia/BristolMeyers Squibb); carboplatin (Paraplatin, BristolMyers Squibb); temozolominde (Temodar) and oxaliplatin (SanofiSynthelabs).

Antiandrogens such as flutamide (Eulexin, AstraZeneca); nilutamide (Anandron, Aventis); bicalutamide (Casodex, AstraZeneca).

Antiestrogens such as tamoxifen (Nolvadex, AstraZeneca); toremofine (Fareston, Orion/Shire); Faslodex (AstraZeneca); arzoxifene (Eli Lilly & Co.); Arimidex (AstraZeneca); letrozole (Femera, Novartis); Lentaron (Novartis); Aromasin (Pharmacia); Zoladex (AstraZeneca); lasoxifene (CP366,156, Pfizer); ERA92 (Ligand/Wyeth); DCP 974 (DuPont/Bristol Myers Squibb); ZK 235253 (Shering AG); ZK1911703 (Shering AG); and ZK 230211 (Shering AG);

Oncogene Activation Inhibitors, including for example, BcrAbl Kinase Inhibition such as Gleevec (Novartis); Her2 Inhibition such as trastuzumab (Herceptin, Genentech); MDX 210 (Medarex); E1A (Targeted Genetics); ME103 (Pharmexa); 2C4 (Genentech); C11033 (Pfizer); PKI 166 (Novartis); GW572016 (GlaxoSmithKline) and ME104 (Pharmexa); EGFr Inhibitors such as Erbitux (Imclone/BristolMyers Squibb/Merck KgaA); EGFr Tyrosine Kinase Inhibitors such as gefitinib (Iressa ZD 1839, AstraZeneca); cetuximab (Erbitux, Imclone/BMS/Merck KGaA); erlotinib (Tarceva, OSI Pharmaceutical/Genentech/Roche) ABXEGF (Abgenix); C11033 (Pfizer); EMD 72000 (Merck KgaA); GW572016 (GlaxoSmithKline); EKB 569 (Wyeth); PKI 166 (Novartis); and BIBX 1382 (Boehringer Ingleheim); Farnesyl Transferase Inhibitors such as tipifamib (Zarnestra, Johnson & Johnson); ionafarnib (Sarasar, ScheringPlough) BMS214,662 (BristolMyers Squibb); AZ3409 (AstraZeneca); CP609,754 (OSI Pharmaceuticals); CP663,427 (OSI Pharmaceuticals/Pfizer); Arglabin (NuOncology); RPR130401 (Aventis); A 176120 (Abbott); BIM 46228 (Biomeasure); LB 42708 (LG Chem); LB 42909 (LG Chem); PD 169451 (Pfizer); and SCH226374 (Schering-Plough); Bcl2 Inhibitors such as BCLX (Isis); ODN 2009 (Novartis); GX 011 (Gemin X); and TAS 301 (Taiho); Cyclin Dependent Kinase Inhibitors such as flavopiridol (generic, Aventis); CYC202 (Cyciacel); BMS 387032 (BristolMyers Squibb); BMS 239091 (BristolMyers Squibb); BMS 250904 (BristolMyers Squibb); CGP 79807 (Novartis); NP102 (Nicholas Piramal); and NU 6102 (AstraZeneca); Protein Kinase C Inhibitors such as Affinitac (Isis, Eli Lilly & Co.); midostaurin (PKC 412, Novartis/generic); bryostatin (NCI/GPC Biotech/generic); KW 2401 (NCI/Kyowa Hakko); LY 317615 (Eli Lilly & Co.); perifosine (ASIA Medica/Baxter/generic); and SPC 100840 (Sphinx);

Telomerase Inhibitors such as GRN163 (Geron/Kyowa Hakko) and G4T 405 (Aventis); Antibody Therapy including Herceptin (Genentech/Roche); MDXH210 (Medarex); SGN15 (Seattle Genetics); H11 (Viventia); Therex (Antisoma); rituximan (Rituxan, Genentech); Campath (ILEX Oncology/Millennium/Shering); Mylotarg (Celltech/Wyeth); Zevalin (IDEC Pharmaceuticals/Schering); tositumomab (Bexxar, Corixa/SmithKline Beecham/Coulter); epratuzumab (Lymphocide, Immunomedics/Amgen); Oncolym (Techniclone/Schering AG); Mab Hu1D10 antibody (Protein Design Laboratories); ABXEGF (Abgenix); inflex-imab (Remicade®, Centocor) and etanercept (Enbrel, WyethAyerst).

Antipsoriasis Agents such as anthralin; vitamin D3; cyclosporine; methotrexate; etretinate, salicylic acid; isot-retinoin; and corticosteroids; Antiacne Agents such as ret-inoic acid; benzoyl peroxide; sulfurresorcinol; azelaic acid; clendamycin; erythromycin; isotretinoin; tetracycline; minocycline; Antiskin parasitic Agents such as permethrin and thiabendazole; Treatments for Alopecia such as minoxi-dil and finasteride; Contraceptives such as medroxyproges-terone; norgestimol; desogestrel; levonorgestrel; norethin-drone; norethindrone; ethynodiol; and ethinyl estradiol; DNAalkyltranferase Agonist including temozolomide; Met-alloproteinase Inhibitor such as marimastat; Agents for management of wrinkles, bladder, prostatic and pelvic floor disorders such as botulinum toxin; Agents for management of uterine fibroids such as pirfenidone, human interferinal-pha, GnRH antagonists, Redoxifene, estrogenreceptor modulators; Transferrin Agonist including TransMID (Xenova Biomedix); TfCRM107 (KS Biomedix); Interleukin13 Receptor Agonist such as IL13PE38QQR (Neopharm); Nucleic acids such as small interfering RNAs (siRNA) or RNA interference (RNAi), particularly, for example siRNAs that interfere with VEGF expression; and Psychotherapeutic Agents including Antianxiety drugs such as chlordiazepox-ide; diazepam; chlorazepate; flurazepam; halazepam; praze-pam; clorazepam; quarzepam; alprazolam; lorazepam; ora-zepam; temazepam; and triazolam; and Antipsychotic drugs such as chlorpromazine; thioridazine; mesoridazine; trifluo-rperazine; fluphenazine; loxapine; molindone; thiothixene; haloperidol; pimozide; and clozapine.

Consideration of Forming Solid Phase within a Gel

Solid phase can be added to a formed gel or fixed within a gel during polymerization of the pregel liquid state to a gel state. Solid phase can be formed within a gel. The present invention provides a novel process for producing solid materials based on synthetic polymers and/or biopolymers, in which the synthetic polymers and/or biopolymers are dissolved or dispersed in ionic liquids, optionally together with additives, the synthetic polymers and/or biopolymers are regenerated as solids by contacting the resulting solution or dispersion with a further liquid or gel which is miscible with the ionic liquid but is incapable of dissolving the solid synthetic polymers and/or biopolymers, and freeing the resulting regenerated solids from the synthetic polymers and/or biopolymers of the ionic liquids and the further liquid, which results in the solid materials based on synthetic polymers and/or biopolymers.

Accordingly, the present process for producing solid materials within gels has the following process steps: (1) solubilizing at least one solid polymer and/or biopolymer (A), or at least one synthetic polymer and/or biopolymer (A) and at least one additive (B), in at least one substantially or completely anhydrous chaotropic liquid (C), (2) contacting the solution or dispersion (AC) or (ABC) obtained in process step (1) with a gel (G) which is miscible with the chaotropic liquid (C), but in which at least the synthetic polymer and/or the biopolymer (A) are substantially or completely insoluble, which results in a solid phase (P) which comprises or consists of solid synthetic polymer and/or biopolymer (A), chaotropic liquid (C) and gel (G), and if appropriate the at least one additive (B), and a gel phase (G) which comprises or consists of chaotropic liquid (C) and gel (G), (3) removing the chaotropic liquid (C) from phase (G), which results in a multiphasic gel (PG) based on synthetic polymer and/or biopolymer (A), (5) impregnating the multiphasic gel (PG) with a liquid (W) which is miscible both with the chaotropic liquid (C) and with the gel (G), but in which at least the synthetic polymer and biopolymer (A) are substantially or completely insoluble, and (6) removing the two liquids (C) and (W) from the multiphasic gel (PG) by evaporating.

The solid materials may have a wide variety of different threedimensional forms, sizes and morphologies. For instance, they may be pulverulent, in which case the powder particles may have the form of slabs, spheres, drops, rods, cylinders, needles, flakes, or irregularly shaped particles, especially pellets and tori. These bodies may be more or less compact or highly porous, and may have a high internal surface area.

The particle size thereof may vary widely. It may be in the range from a few nanometers up to 1 mm. The particle size distributions may be monomodal or multimodal and range from very broad to very narrow, preferably very narrow, distributions.

The solid materials may, however, also be macroscopic particles, i.e. particles with a greatest diameter of >1 mm. They have essentially the same forms as the powder particles.

In addition, the solid materials may have the form of fibers. These may have different lengths, for example from about 5 mm to highly entangled and different thicknesses, for example 1 micron to 1 mm.

The solid materials may also be provided as films. These may have different thicknesses, for example between 500 nm and 1 mm. The films may be essentially compact, nanoporous, microporous, macroporous or in the form of sponge. The films are preferably essentially compact.

In particular, the solid materials are powders. The powder particles preferably have a mean particle size measured by sedimentation in a gravitational field of 100 microns to 3 mm, preferably 200 microns to 2.5 mm and especially 300 microns to 2 mm.

For the performance of the process according to the invention, basically all synthetic polymers and/or biopolymers (A) are suitable, provided that they are soluble in one of the chaotropic liquids (C) described and insoluble in the gel (G) and liquid (W). In terms of method, the solubilization in the first process step has no special features, and can be performed with the aid of the customary and known mixing units, such as stirred tanks, Ultraturrax, inline dissolvers, homogenization units such as homogenization nozzles, kneaders or extruders, continuously or in batchwise mode.

The content of polymers (A) in the solution or dispersion (AC) or (ABC) which results in the first process step can likewise vary widely. In general, the upper limit of the content is fixed in the individual case by the fact that the viscosity of the solution or dispersion (AC) or (ABC) in question must not become so high that it can no longer be processed. The content is preferably 0.1 to 50% by weight, more preferably 0.25 to 30% by weight and especially 0.5 to 20% by weight, based in each case on (AC) or (ABC).

Later in the process according to the invention, in the second process step, the solution or dispersion (AC) or (ABC) obtained in the first process step is contacted with a gel (G). The gel (G) is miscible with the abovedescribed chaotropic liquid (C), preferably without a miscibility gap, i.e. in any quantitative ratio. In contrast, the polymer (A) is substantially or completely insoluble in (G). Any additives (B) present may be soluble or insoluble in (G).

The chaotropic liquid (C) used is preferably acetone, methanol, ethanol, propanol, butanol, ethylene glycol, propylene glycol, diethylene glycol, 2methoxyethanol, 2ethoxyethanol, 2propoxyethanol and/or 2butoxyethanol, the nitrile used is preferably acetonitrile and/or propionitrile, the ether used is preferably diethyl ether, dipropyl ether, tetrahydrofuran and/or dioxane, the ketone used is preferably acetone and/or methyl ethyl ketone, the aldehyde used is preferably acetaldehyde and/or propionaldehyde, the sulfoxide used is preferably dimethyl sulfoxide, and the amide used is preferably dimethylformamide, acetamide and/or hexamethylphosphortriamide.

Particular preference is given to using strongly protic and aprotic polar organic liquids which already have a comparatively high vapor pressure or a boiling point below 100 degree C. as the liquid (C).

Very particular preference is given to using ethanol and/or water, but especially water, as the liquid (W)

The solution or dispersion (AC) or (ABC) can be contacted in different ways with gel (G), for example by pouring, dripping or extruding the solution or dispersion (AC) or (ABC) into the gel (G), or contacting it in the form of a film with gel (G). This can be performed continuously or in batchwise mode. The quantitative ratio of solution or dispersion (AC) or (ABC) to gel (G) may vary widely from case to case. It is essential that the quantitative ratio is selected such that the polymer (A) is precipitated or regenerated quantitatively. The person skilled in the art can therefore easily determine the quantitative ratio required on the basis of his or her general technical knowledge, if appropriate with the aid of a few preliminary tests.

The temperature at which the second process step is performed can likewise vary widely. The temperature is guided primarily by the temperature range within which the gel (G) is in a fluidlike state. The solution or dispersion (AC) or (ABC) should also not have excessively high temperatures on contact with (G), because the result may otherwise be abrupt evaporation and/or decomposition of the gel (G) or polymer (A). The second process step is preferably likewise performed at temperatures of 0 to 100 degree C., more preferably 10 to 70 degree C., especially preferably 15 to 50 degree C. and especially 20 to 30 degree C. In the second process step, the result is a solid phase which comprises or consists of solid polymer (A), chaotropic liquid (C) and gel (G), and if appropriate the at least one additive (B), and also a liquid phase (W) which comprises or consists of chaotropic liquid (C) and gel (G).

Later in the process according to the invention, in the fourth process step, the chaotropic liquid (C) is removed from phase (PG) with the aid of the liquid (W), which results in a gel (PG) based on the polymer (A). Preference is given to removing the chaotropic liquid (C) by extracting phase (W) by washing at least once with the liquid (W), and the wash liquid (W) is then removed from phase (PG). This can be done by employing the abovedescribed continuous or batchwise method. The washing and removal are preferably continued until chaotropic liquid (C) can no longer be detected in the gel (PG) and/or in the wash liquid (W).

Preferably, the fourth process step is performed at temperatures at which the resulting gel (PG) is not thermally damaged, more particularly does not age rapidly. Preference is given to employing temperatures of 0 to 100 degree C., more preferably 10 to 70 degree C., especially preferably 15 to 50 degree C. and especially 20 to 30 degree C. The resulting gel (PG) preferably already essentially has the appropriate threedimensional form, like the solid material based on polymers (A) to be produced therefrom.

Later in the process according to the invention, in the fifth process step, the gel (PG) is treated with a liquid (VV) which is miscible with the chaotropic liquid (C) and with the gel (G), but in which at least the polymer (A) is substantially or completely insoluble.

When, for example, water is used as the liquid (W) which is particularly preferred in accordance with the invention it is possible to use all of the above described strongly protic and aprotic polar organic liquids which have a higher vapor pressure than water or a boiling point below 100 degree C. at standard pressure.

Later in the process according to the invention, in the sixth process step, the two liquids (C) and (W) are removed from the gel (PG) by evaporating or fractionation. Preference is given to fractionation comparatively slowly under gentle conditions at standard pressure or a slightly reduced pressure between 50 and 100 kPa. Preference is given to employing temperatures between 20 and 50 degree C. More particularly, the fractionation is effected at room temperature and under standard pressure.

Apart from the sixth process step, it is possible to perform at least one of the process steps of the process according to the invention at a pressure greater than 100 kPa. Preference is given to performing the process according to the invention at standard pressure overall. Owing to the exact adjustability of the dimensions thereof of the solid phase, the resulting solid materials based on synthetic polymers and/or biopolymers (A), especially of absorbable polyurethanes (A), can be joined in a process specific way, in a secure and reliable manner, to give even more complex threedimensional moldings.

By virtue of the abovedescribed additives (B), the resulting solid materials based on synthetic polymers and/or biopolymers, especially on absorbable polyurethanes (A), can be modified in a wide variety of different ways for the inventive use. The additives (B) may be present in more or less homogeneous distribution in the polymer (A) matrix of the solid materials produced with the aid of the process according to the invention. For example, it may be advantageous when fibrous additives (B) have an inhomogeneous distribution, in order to vary mechanical properties in a desired manner. The situation is similar for catalytically active additives (B), the accessibility of which in the polymer (A) matrix can be improved by an inhomogeneous distribution. In many cases, however, a very substantially homogeneous distribution in the polymer (A) matrix is advantageous, for instance when plasticizing additives (B) are used.

The additives (B) may be bonded in a more or less fixed manner to the polymer (A) matrix of the solid materials produced with the aid of the process according to the invention. For instance, especially polymeric or particulate additives (B) may be bonded permanently to the polymer (A) matrix. In contrast, especially in the case of the low molecular weight additives (B), it may be advantageous when they are not bonded permanently to the polymer (A) matrix, and are instead released again in the manner of a slow release or controlled release.

The multiphasic gels which are based on synthetic polymers and/or biopolymers (A), and also on polysaccharides (G), and are produced in the inventive procedure can therefore be used advantageously in a wide variety of different technical fields in the context of the inventive use. For instance, they can be used in synthetic and analytical chemistry, biochemistry and gene technology, biology, pharmacology, medical diagnostics, cosmetics, natural gas and mineral oil extraction technology, process technology, paper technology, packaging technology, electrical engineering, magnet technology, communications technology, broadcasting technology, agricultural technology, aviation and space technology and textile technology, and also construction, land and sea transport and mechanical engineering, especially as construction materials, insulations, fabric, absorbents, adsorbents, membranes, separating materials, barrier layers, controlled release materials, catalysts, cultivation media, catalysts, and also coloring, fluorescent, phosphorescent, electrically conductive, magnetic, microwaveabsorbing and flameretardant materials, or for the production thereof.

EXAMPLES

The following are examples provided to illustrate the method and multiphasic systems of the present invention. The constituents of the following examples are available from SigmaAldrich, unless otherwise indicated. In some cases equivalent weights are used rather than gram amounts. When equivalent weights are used, the equivalent is defined with respect to a functional group, for example hydroxyl groups, isocyanate groups, amine groups and the like. The relevant functional group should be obvious to one skilled in the art of the synthesis of polymeric gels. When the word "equivalent" is used, it is meant equivalent weight.

Coupling Solid and Gel Phases

Aforementioned, solid phase can be inserted mechanically into an existing gel phase, the gel state can be formed around a distribution of solid phase, the solid phase can be formed within an existing gel state, or in either of these cases the solid phase and gel phase chemically interact to form bonds.

The solid and gel phases are typically characterized as possessing pendant hydroxyl groups. When a desired distribution of solid phase and gel phase is obtained to form a multiphasic gel, this state of distribution can be fixed by addition of a crosslinker, for example a diisocyanate.

Alternatively, the solid or gel phases can possess a surplus of terminal NCO groups such that when one of the gel or solid phases possessing terminal hydroxyl groups is introduced into the state possessing terminal isocyanate groups that spontaneous polymerizations occurs. This polymerization can be enhanced by the addition of catalysts known in the art. The polymerization that occurs is local, and limited to bonds formed between gel phase molecules and solid phase molecules. In this situation, it is preferred that the distribution of solid phase be sufficiently diffuse that chain extension or polymerization between solid phase structures does not occur, unless a more complex solid phase geometry desired.

The form of macroscopic crosslinking can achieve any degree desired of constraint on the overall multiphasic gel system. For example, the coupling can be strictly local between discrete solid phase and gel domains. Alternatively, and especially with diffusion of soluble hydroxyl rich monomers in the gel matrix, chain extension can occur, especially if the isocyanate functionality is not localized to either the gel phase or the solid phase. If hydroxyl rich monomers are to be used in the final fixing of solid state relative to gel state, than any unreacted monomers are to be washed out by the use of a suitable polar solvent, such as water. It is important that the resulting multiphasic gel system be cohesive. In particular, there should be no free small molecule constituents that are not intended to provide a biofunctional aspect. Conversely, no fixing of the gel phase to the solid phase, preferably, alters the functionality or distribution mechanics of a molecular biofunctional constituent intended to be released into a mammalian body.

Example 1

Solid Phase A

In a 3neck flask are placed 400 g of a PLADiol (Mn=1000) and 200 g of Terathane 2000 (Invista, Wichita, Kans.). Toluene is added in excess, and the mixture gently heated to remove toluene to obtain a 20% w/w solution. After cooling to room temperature, 650 g of isophorone diisocyanate was added and mixed under dry nitrogen. To the mixture was then added 5 g of dibutyltindilaurate (DBTL) and the mixture was heated to 75 .degree.C. After 5 hours, 128.7 g of 1,4butane diol is added and the reaction mixture is diluted with toluene to get concentration of all components of approximately 15% Subsequently, the temperature is raised to 80.degree.C. After 10 hours the mixture is allowed to cool to room temperature. The toluene is driven off under vacuum until a clear solid polyurethane is obtained.

Example 2

Solid Phase B

In a 3neck flask are placed 400 g of a PLADiol (Mn=1000) and 400 g of polyethylene glycol (Mn=2000). Toluene is added in excess, and the mixture gently heated to remove toluene to obtain a 20% w/w solution. After cooling to room temperature, 650 g of isophorone diisocyanate was added and mixed under dry nitrogen. To the mixture was then added 5 g of dibutyltindilaurate (DBTL) and the mixture was heated to 75 degrees C. After 5 hours, 128.5 g of 1,4butane diol is added and the reaction mixture is diluted with toluene to get concentration of all components of approximately 15% Subsequently, the temperature is raised to 80.degree.C. After 10 hours the mixture is allowed to cool to room temperature. The toluene is driven off under vacuum until a clear solid polyurethane is obtained.

Example 3

Solid Phase C

In a 3neck flask was placed 200 g of a PLADiol (Mn=2000), 200 g of polycaprolactone (Mn=2000) and 400 g of polyethylene glycol (Mn=2000). Toluene is added in excess, and the mixture gently heated to remove toluene to obtain a 20% w/w solution. After cooling to room temperature, 505 g of isophorone diisocyanate was added and mixed under dry nitrogen. To the mixture was then added 7 g of dibutyltindilaurate (DBTL and the mixture was heated to 75 degrees C. After 5 hours, 128.5 g of 1,4butane diol is added and the reaction mixture is diluted with toluene to get concentration of all components of approximately 15%. Subsequently, the temperature is raised to 80 degrees C. After 10 hours the mixture is allowed to cool to room temperature. The toluene is driven off under vacuum until a clear solid polyurethane is obtained.

Example 4

Solid Phase D

Pluronic 31R1 (molecular weight 3250) (BASF, Mt. Olive, N.J.) was dried under vacuum at 85.degree. C. for 12 hr. in a spherical flask, the final water content obtained was below 300 ppm. One equivalent of Pluronic 31R1 was added to ⅕ equivalent (l) Lactide and 0.18 grams catalyst (stannous 2ethyl hexanoate) (0.43%). The reaction was carried out in a sealed flask, under a dry nitrogen saturated atmosphere, for two and half hours at 145 degrees C. To the above synthesis is added 2 equivalents of toluene diisocyanate and reacted at 60 degrees C. for 8 hours. To this result is added ½ equivalent of biofunctional molecule, for example a *boswellia* extract and reacted at 75 degrees C. for 8 hours.

Example 5

Solid Phase E

Polyethylene glycol (molecular weight 3000) was dried in vacuo overnight at 85.degree. C. Thereafter, the PEG was cooled down to room temperature, and the product capped with dry nitrogen. One equivalent of PEG was added to ⅕ equivalent (1) Lactide and 0.18 grams catalyst (stannous 2ethyl hexanoate). The mixture of PEG and lactide is placed in an oil bath under flowing nitrogen at 140 degree C. and mixed for 3 hours. To the above synthesis is added 2 equivalents of toluene diisocyanate and reacted at 60 degrees C. for 8 hours. To this result is added ½ equivalent of biofunctional molecule, for example a *boswellia* extract and reacted at 75 degrees C. for 8 hours.

Example 6

Solid Phase F

In a reactor equipped with stir rod, place 2 moles of diisocyanate under nitrogen. Heat the volume to 60.degree.C and slowly add 1 mole of poloxamer diol. The poloxamer should be added at a rate slow enough such that the volume temperature does not rise above 65.degree.C. If the poloxamer is a solid at 60.degree.C, then a solvent can be used. When all the poloxamer has been added to the reaction volume the mixture should be reacted until the isocyanate content corresponds to two available NCO groups per poloxamer molecule. Adding the poloxamer slowly ensures each poloxamer molecule is endcapped with two diisocyanate molecules, because the majority of the reaction is done in an excess of diisocyanate, and chain extension of the poloxamer is less probable. If prevention of chain extension is important a large excess of diisocyanate can be employed, and the excess diisocyanate evaporated at the termination of the reaction. Once the poloxamer diisocyanate is prepared as described above, 1 mole can be loaded into a reactor under nitrogen, heated to 85.degree.C and two moles of dilactide (A) or more generally an ester added slowly, and as before preventing an excessive exotherm. To this result is added ½ equivalent of biofunctional molecule, for example a *boswellia* extract and reacted at 75 degrees C. for 8 hours.

Example 7

Gel Phase A

While poloxamers of many varied combinations of ethylene oxide (B) and propylene oxide (C) are commercially available, there are practical limits on constructing these chains with monomeric ethylene oxide and propylene oxide. Greater control is afforded by starting with diisocyanates (D) of the monomers, for example DBD or DCD. To these B or C can be arbitrarily added in any combination by forming urethane links between the addition monomer and the diisocyanate end capped chain. Through a stepwise sequence of chain extensions with monomers and subsequent end capping with diisocyanate and combination of B and C can be obtained. One drawback is that the resulting polymer will be more hydrophobic that a chain obtained by direct polymerization of ethylene oxide and propylene oxide. However, this drawback can be compensated in most cases by using less propylene glycol.

Multiarmed polymers can be constructed without cross-linking by introducing a triol (T) and linking the triol to poloxamer chains with diisocyanate. For example, poloxamer chains are introduced into a reactor and endcapped with diisocyanate. The resulting poloxamer diisocyanate is then reacted with a low molecular weight triol such a trimethylolpropane. The result is a poloxamer triisocyanate which then can be reacted with ester (A). Preferably, the ester is polylactic acid. This yields a gel prepolymer. Gels can be made by adding water and stirring vigorously. Gels comprising up to 95% water can be made.

Example 8

Gel Phase B

The prepolymer of EXAMPLE 7 wherein the polylactic acid is substituted with sodium hyaluronan. Gels can be made by adding water and stirring vigorously. Gels comprising up to 95% water can be made.

Example 9

Gel Phase C

The prepolymer of EXAMPLE 7 wherein the polylactic acid is substituted with any of the above Solid Phases Example 10

Method of Adding Hyaluronan to a Gel Prepolymer

Hyaluronan contains repeating segments of $C_{14}H_{21}NO_{11}$, each containing 5 hydroxyl groups (OH). To form a diisocyanate of hyaluronan one reacts a quantity of diisocyanate containing 2 moles of NCO greater than the number of moles of OH. Thus, a hyaluronan containing 1 unit of C 14 H 21 NO 11 per molecule, then 1 mole of hyaluronan molecules if to be reacted with 7 moles of diisocyanate. The reaction is performed in an organic solvent, where the hyaluronan is altered by ammonia to make it soluble in an organic solvent, for example tetrahydrofuran. A small amount of tin catalyst is added to promote urethane link formation between the hydroxyls of the hyaluronan and the isocyanate groups of the diisocyanate. To discourage chain extension, the hyaluronan is first dissolved in organic solvent and set aside. The reactor is charged with catalyst and diisocyanate and heated to 80 degrees C. The hyaluronan solution is slowly added to the reactor and the exotherm monitored. Complete reaction is indicated when the exotherm subsides. Alternatively, one can measure the % NCO at each step to verify all the hydroxyl groups on the hyaluronan are endcapped with isocyanate. When all the hyaluronan is added to the reactor the reaction is run until the desired % NCO is reached. % NCO is measured by conventionally by dibutylamine titration. The reaction is complete when 2 moles of NCO are measured for every mole of product molecule. Ideally there is only 1 C 14 H 21 NO 11 unit per product molecule. However, in other applications a spectrum of product molecules containing a range of C 14 H 21 NO 11 unit per product molecule is desired. The desired polydispersity can be obtained by adjusting the amount of NCO used, and verifying with GPC and % NCO measurements.

In any one reaction, the dispersity of molecular weights of product molecules will be Gaussian around a desired mean. Multimodal distributions can be obtained by mixing the reaction product of multiple reactions. Hyaluronan isocyanates of higher isocyanate functionality can be synthesized by adjusting the ratio of OH groups to isocyanate groups in the reaction mix.

Example 11

Gel Phase D

In this example a castorderived hydroxylterminated ricinoleate derivative is used as the triol. One equivalent of polycin T400 (141 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=13.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (282 Dalton+2×174 Dalton) yielding approximately 13.3%. The above reaction will yield a viscous product. A less viscous product can be obtained by adding propylene carbonate to the initial mixture. Additions up to 100% by weight of propylene carbonate are useful. Adjustment to the target NCO of the mixture must be performed using standard methods, or the propylene carbonate may be added after reaching the target % NCO. Propylene carbonate is available from SigmaAldrich (Milwaukee, Wis.).

Example 12

Gel Phase E

In this example a polyether hydroxylterminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (3×42 Dalton) per product molecule by the total weight of the product molecule (9199 Dalton+3×174 Dalton) yielding approximately 1.3%. Multranol 9199 is available from Bayer (Pittsburgh, Pa.).

Example 13

Gel Phase F

Any of the diisocyanates prepared above can be trimerized by the addition of a low molecular weight triol such as polycin T400 or trimethylolpropane (TMP). In this example TMP is used, but the method is adaptable to any triol. Complete trimerization of the diisocyanates of Example 1 and 2 will result in viscous products. To yield a lower viscosity product propylene carbonate can be employed or less triol can be used. In the latter case, a mixture of diisocyanate and triisocyanate is obtained.

In this example the preceding polyether diisocyanate is used. One equivalent of polyether diisocyante (682 g) is combined with 0.1 equivalent TMP (44.7 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=5.8%. The target % NCO is reached when every hydroxyl group in the mixture is reacted with an NCO group. The ideal % NCO is calculated by dividing the weight fraction of the functional isocyanate groups 10%(3×42 Dalton) and 90%(2×42) per product molecule by the total weight fraction of the product molecule (3×1364 Dalton+134 Dalton)+1364 yielding approximately 0.3%+5.5%=5.8%. TMP is available from SigmaAldrich (Milwaukee, Wis.).

Example 14

Preparation of a Modified *Boswellia* Extract Using a Triisocyanate

The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

One hundred grams of the preceding polyether triisocyanate is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Example 15

Preparation of Modified *Boswellia* Extract Using a Triisocyanate

Preparation of a modified *Boswellia* extract using the triisocyanate/diisocyanate of Example 14.

The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0. In this example the product of Example 14 is used as the polyether diisocyanate/triisocyanate mixture. One hundred grams of Example 29 is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Example 16: Preparation of Modified *Boswellia* Extract Using Multibranched Isocyanate Preparation of a Polyether Triisocyanate In this example a polyether hydroxylterminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored.

The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (3×42 Dalton) per product molecule by the total weight of the product molecule (9199 Dalton+3×174 Dalton) yielding approximately 1.3%. Multranol 9199 is available from Bayer (Pittsburgh, Pa.).

Preparation of a Modified *Boswellia* Extract Using the Above Triisocyanate.

The hydroxyl number of *Boswellia* extract will vary depending on extraction method, species of *Boswellia* extracted, and even variations within species. The goal is to obtain a product with no NCO functionality, so all reaction mixtures should be reacted until the final % NCO=0.

One hundred grams of above triisocyanate is combined with 1 g of *Boswellia* extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of *Boswellia* extract is to be added. By a series of *Boswellia* addition one calculates the change in % NCO as a function of 1 g additions of *Boswellia* extract, a linear plot is obtained from which the total amount of *Boswellia* extract addition necessary to bring the % NCO to zero is obtained. This amount of *Boswellia* extract is added to the mixture and the mixture is reacted so that % NCO=0 is obtained.

Example 17

Preparation of Genus 1 Solid Phase

Any of the above solid phase absorbable polyurethanes may be used. The polyurethane is dissolved in acetone in a 20% by weight ratio of polymer to acetone to form a polyurethane solution. A beaker is filled with distilled water and placed on a magnetic stirrer. The stir rate is selected to create a vortex in the water. A 3 ml syringe with an 18G needle is loaded with polyurethane solution. The tip of the needle is placed in the water and the polyurethane solution is introduced into the water at a rate of 1 ml/minute.

The polyurethane instantly becomes a solid on contact with the water. The lamellar flow of the polyurethane solution through the inner diameter of the needle induces a rolling motion at the exit of the needle. The solidifying polyurethane forms into tori upon exit of the needle. The rate of introduction of the polyurethane solution to the water can be used to control the thickness of the formed tori. Other variables that can be adjusted are the temperature of the water, the dilution of the polyurethane solution, and the selection of solvents other than acetone. The diameter of the formed tori can be controlled by selecting needles of different inner diameter. Small inner diameter results in small diameter tori.

After each introduction of 3 ml of polyurethane solution to 100 ml of water, the stirring of the water is halted. The water at this point appears milky with homogenously distributed microtori. During this standing period the acetone is drawn out of the polyurethane by the water. A period of approximately 1 hour is allocated for the acetone to leave the polyurethane sufficiently to prevent clumping and adhesion of the tori. The tori may be filter from the water suspension, or another bolus of polyurethane solution may be administered. Up to approximately 15 ml of polyurethane solution can be introduced into the water if single tori are desired. Higher genus solid phase can be obtained by allowing the tori density to increase to the point where newly formed tori have a high probability of joining with an existing torus in solution while the introduced polyurethane is still in a relatively solvated state.

Figure 4:
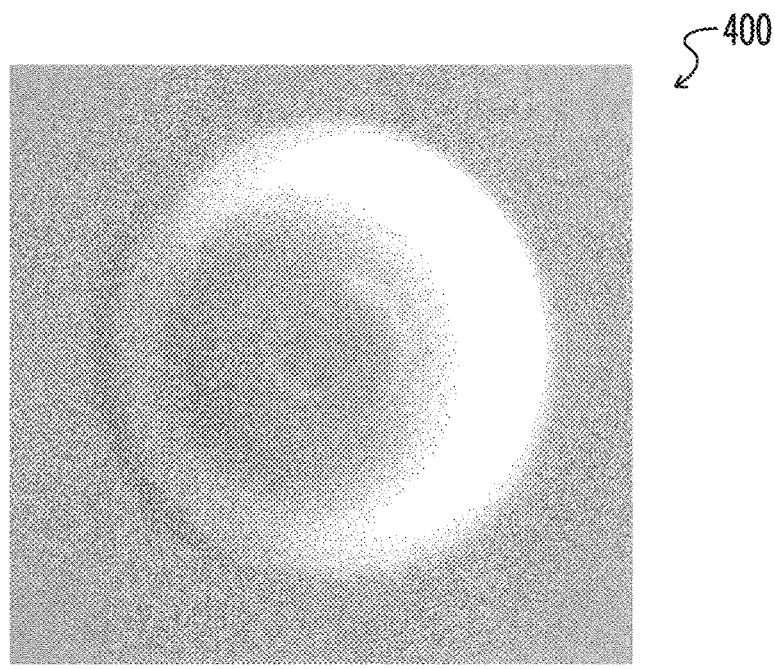
FIG. 4 is an image of a toroid multiphase gel structure according to the present disclosure.

Tori can be harvested from solution using standard filter paper, wherein the tori are captured on the filter paper and dried in an oven at 40° C. The result is dry, flowable tori. An image of a torus 400 prepared according to the present methods is shown in FIG. 4. Torus 400 has a diameter of about 500 micron.

Example 18

Formation of a Multiphase Gel

Any of the above gel prepolymers can be used. A beaker of water is charged with a desired density of solid phase tori and stirred at a rate sufficient to obtain a uniform distribution of tori in the water. A solution of gel prepolymer is prepared by making a solution of prepolymer and a solvent. Solvents can be acetone, toluene or an inert addition such as propylene carbonate or a water miscible diol. The solution is introduced to the water mixture at 1 cc/minute at 10 minute intervals. Between intervals the pH of the solution is maintained between 6.5 and 7.5 pH using a suitable base, for example sodium hydroxide. This process is continued until a desired viscosity is achieved. Slower additions are successful, but faster additions may result in the formation of inhomogeneities in the forming gel. The formed gel is then washed in distilled water several time to remove the solvent and sodium ions. If a volatile solvent is used, vacuum can be used to remove solvent. It is important that the gel does not desiccate, since many gels will not rehydrate fully.

Example 19

Formation of a Rehydrating Multiphase Gel

In some instances it is desirable to obtain a multiphase gel which can have all the water removed and be rehydrating to its originally formed ratio of water to polymer. To achieve this result, the water fraction of the gel can be loaded with salt ions, in particular sodium chloride. Under rehydration, reintroduction of the dehydrated gel to distilled water in a ratio of polymer weight to water volume that will result in 0.9% salt (physiologic saline) is useful in implantable applications.

Although there have been described particular embodiments of the present invention of a new and useful MULTIPHASE GEL it is not intended that such references be construed as limitations upon the scope of this invention except as set forth in the following claims.

What is claimed is:

1. The reaction product of:
   a gel phase comprising a poloxamer polymer backbone to which is linked hyaluronan groups, the polymer backbone being endcapped with two diisocyanate molecules, and
   a torus shaped solid phase comprising a polyurethane, wherein the gel phase and solid phase are coupled by mechanical forces or chemical bonds.

2. The composition of claim 1, wherein the solid and gel phases are coupled by mechanical forces.

3. The composition of claim 1, wherein the solid and gel phases are coupled by chemical bonds.

4. A composition of claim 1, wherein the solid phase and gel phase are coupled by a polysaccharide.

5. The composition of claim 1, wherein the solid phase is distributed in the gel phase, and wherein the dimensional freedom on the gel phase is reduced by the solid phase.

6. The composition of claim 1, wherein all the constituents are absorbed by a mammalian body when implanted in a mammalian body.

7. The composition of claim 1, wherein at least one of the gel phase or the solid phase contains a biofunctional molecule.

8. The composition of claim 1, wherein at least one of the gel phase or the solid phase, or both in combination, block the formation of tissue adhesions between layers of tissue between which said composition is disposed.

9. The composition of claim 1, wherein the gel phase blocks tissue adhesions and the solid phase provides a biofunctional aspect.

10. The composition of claim 1, wherein the gel phase is resorbed before the solid phase.

11. The composition of claim 1, wherein the gel phase or the solid phase, or both, comprise a biologically active agent.

12. The composition of claim 1, wherein the composition forms a contiguous mass, and the contiguous mass is entirely bioresorbable, and no volumetric division of dimension greater than one cubic micron of said composition separates from said contiguous mass at any time during bioresorption.

13. The composition of claim 1, wherein the solid phase comprises a surface texture wherein the surface texture comprises a plurality of protrusions, a plurality of depressions, or a combination of a plurality of both protrusions and depressions.

14. The composition of claim 1, wherein the gel phase is resorbed at a faster rate than the solid phase, the solid phase possesses surface texture, and the resorption of the gel phase exposes the surface texture of the solid phase.

* * * * *